United States Patent
Rovatti et al.

(10) Patent No.: US 12,336,846 B2
(45) Date of Patent: Jun. 24, 2025

(54) NON-INVASIVE SENSOR FOR DETERMINING A HEARTBEAT AND/OR HEART RATE IN A SEGMENT OF AN EXTRACORPOREAL BLOOD CIRCUIT

(71) Applicant: Gambro Lundia AB, Lund (SE)

(72) Inventors: Paolo Rovatti, Finale Emilia (IT); Mariano Ruffo, Naples (IT); David Stefani, Modena (IT)

(73) Assignee: Gambro Lundia AB, Lund (SE)

( * ) Notice: Subject to any disclaimer, the term of this patent is extended or adjusted under 35 U.S.C. 154(b) by 493 days.

(21) Appl. No.: 17/761,318

(22) PCT Filed: Sep. 18, 2020

(86) PCT No.: PCT/EP2020/076200
§ 371 (c)(1),
(2) Date: Mar. 17, 2022

(87) PCT Pub. No.: WO2021/053201
PCT Pub. Date: Mar. 25, 2021

(65) Prior Publication Data
US 2022/0249025 A1  Aug. 11, 2022

(30) Foreign Application Priority Data

Sep. 19, 2019 (EP) .................................... 19198444
Sep. 19, 2019 (IT) ........................ 102019000016787

(51) Int. Cl.
*A61B 5/00* (2006.01)
*A61B 5/024* (2006.01)
(Continued)

(52) U.S. Cl.
CPC ........ *A61B 5/6866* (2013.01); *A61B 5/02416* (2013.01); *A61B 5/7257* (2013.01);
(Continued)

(58) Field of Classification Search
CPC .............. A61B 5/6866; A61B 5/02416; A61B 5/7257; A61B 5/746; A61B 5/02444;
(Continued)

(56) References Cited

U.S. PATENT DOCUMENTS 4,710,164 A    12/1987  Levin et al.
4,718,891 A     1/1988  Lipps
(Continued)

FOREIGN PATENT DOCUMENTS

AU    2017323136 A1    4/2019
EP       3542707 A1    3/2018
(Continued)

*Primary Examiner* — Gary Jackson
*Assistant Examiner* — Sebastian X Lukjan
(74) *Attorney, Agent, or Firm* — K&L Gates LLP

(57) ABSTRACT

Non-invasive heartbeat sensor for determining a heart rate in a conduit of an extracorporeal blood treatment apparatus, comprising one source for directing an optical signal towards the blood flowing in the segment; one detector for receiving an optical informative signal comprising the signal emitted by said source after passing the blood, and emitting respective output signal; a controller receiving the respective output signal and retrieving a heartbeat frequency and a heart rate value, based on the output signal, wherein the informative signal is altered by flow perturbation of the blood partially generated by the flow impulses originated by the heart.

22 Claims, 12 Drawing Sheets

(51) Int. Cl.
  *A61M 1/36*    (2006.01)
  *A61M 60/113*  (2021.01)
  *A61M 60/279*  (2021.01)
  *A61M 60/37*   (2021.01)

(52) U.S. Cl.
  CPC ............ *A61B 5/746* (2013.01); *A61M 1/367* (2013.01); *A61M 60/113* (2021.01); *A61M 60/279* (2021.01); *A61M 60/37* (2021.01); *A61M 2230/06* (2013.01)

(58) Field of Classification Search
  CPC ............ A61B 5/14535; A61B 5/14546; A61B 5/1455; A61B 5/742; A61M 1/367; A61M 60/113; A61M 60/279; A61M 60/37; A61M 2230/06; A61M 1/3621; A61M 2205/3313; A61M 1/36224; A61M 1/16; A61M 1/36225; A61M 2205/18
  See application file for complete search history.

(56) References Cited

U.S. PATENT DOCUMENTS

| | | | |
|---|---|---|---|
| 6,547,740 | B2 | 4/2003 | Sugo |
| 6,878,272 | B2 | 4/2005 | Kawaguchi |
| 6,878,273 | B2 | 4/2005 | Kawaguchi |
| 2003/0032885 | A1 | 2/2003 | Mann |
| 2007/0123760 | A1 | 5/2007 | Scholler et al. |
| 2008/0188728 | A1 | 8/2008 | Neumann et al. |
| 2016/0302735 | A1 | 10/2016 | Noguchi et al. |
| 2018/0078212 | A1 | 3/2018 | Brumfield |
| 2018/0296744 | A1 | 10/2018 | Solem et al. |

FOREIGN PATENT DOCUMENTS

| | | |
|---|---|---|
| EP | 2519145 B1 | 5/2019 |
| JP | H105285218 A | 11/1993 |
| WO | 2011080194 A1 | 7/2011 |
| WO | 2018112354 A1 | 6/2018 |

NON-INVASIVE SENSOR FOR DETERMINING A HEARTBEAT AND/OR HEART RATE IN A SEGMENT OF AN EXTRACORPOREAL BLOOD CIRCUIT

PRIORITY CLAIM

The present application is a National Phase of International Application No. PCT/EP2020/076200, filed Sep. 18, 2020, which claims priority to IT application No. 102019000016787, filed Sep. 19, 2019, and EP Application Serial No. 19198444.2, filed Sep. 19, 2019. The entire contents of each application are incorporated herein by reference and relied upon.

FIELD OF THE INVENTION

The present disclosure belongs to the general field of signal processing and optical measurement of physical quantities. In detail, the invention relates to an apparatus, to a sensor and to a process for determining at least the heartbeat and/or the heartrate.

BACKGROUND ART

In apparatuses for renal care purpose (hemodialysis for chronic renal care or acute renal failure treatments, or during extracorporeal plasma processing e.g., hemodialysis, hemofiltration, hemodiafiltration, plasmapheresis etc.) the hemodynamic parameters of the patient are measured indirectly through the blood lines (e.g.: arterial and venous average pressures with semi-invasive sensors part of the blood line itself) or sporadically with a traditional inflatable cuff which is arranged on the patient arm. Using of a traditional inflatable cuff does not allow for a continuous blood pressure reading, since its operation involves a temporary occlusion of the arteries and veins of the patient's arm. Moreover, measurement is quite uncomfortable and may be painful for the patient making not acceptable to repeat the measure continuously during a dialysis treatment. Through blood pressure cuffs it is also possible to detect heartbeat and/or heart rate, but just during the period of the measurement (lasting about 1 minute). Known semi-invasive pressure sensors are typically installed on the blood line, in a position close to the pump and far from the patient. Those semi-invasive pressure sensors typically are provided with membranes which enter into contact with the blood or fluid circulating in the conduits of the apparatus. Thus, special care in design and in materials chosen for their realization shall be taken in order to reduce the risk of affection to the health of the patient under treatment.

It has been noticed that the pulse the heart provides to the blood while beating decreases in intensity and/or energy along the path from the fistula access towards the conduit up to the apparatus for extracorporeal blood treatment.

Furthermore, the pumps operatively actuated on the apparatus typically produce unwanted pressure peaks (or flow peaks) on the blood or fluid circulating in the conduits, since they are typically pulsating pumps, in particular peristaltic pumps. This results in worsening the precision and reliability of pressure readings because an unwanted noise is always added to the wanted signal; the pressure peaks (or flow peaks) provided by pumps sometimes may be of a magnitude order greater than the magnitude of the heart pulses. Pressure peaks (or flow peaks) provided by the pump are related, in amplitude and/or frequency, to the flow rate of the pump itself. The higher the flow rate is, the faster the pump rotates, and typically the higher is the frequency at which the peaks occur. This is particularly true for peristaltic pumps, whose operation leads to a discontinuous provision of flow rate/pressure in the conduits along the cycle of operation, due to the cyclic compression of a segment of conduit of a blood circuit which plastically is deformed due to the action of the rollers of the pump against a contrasting wall.

It has been further noticed that for typical flow rates involved in blood treatment, in particular dialysis processes, performed through an extracorporeal blood treatment apparatus, frequencies of the peaks provided by the pump are very close to that of the heart rate, which normally—at resting condition—lies between 50 bpm (or typically 60-70 bpm, the first number referring to well-trained athletes) and 100 bpm, resulting approximately in frequencies of peaks lying between some less of 1 Hz and some less of 2 Hz. The fundamental frequency of the peaks provided by the pump is therefore substantially in close relation to that of the heartbeat and sometimes the frequency of the peaks provided by the pump may be substantially superimposed to that of the heartbeat, differing e.g. for some tenths of Hz. It appears clear that without proper procedures, heart rate readings may be substantially adversely affected by the pulses provided by the pump. Some treatments may lead to a reduction of the differential blood pressure between the diastolic and systolic values, so that the effect of the pump pulses is yet still increased.

This detrimental affection may be solved by temporarily stopping the blood pump, i.e., the treatment processes to read out the pulses, but this has the drawback of influencing the apportion of purified blood to the patient, lengthens the treatment, requires a specific configuration for the blood treatment apparatus and anyway does not allow continuous reliable monitoring, since the pump shall be reactivated after a short period of time after the reading. Continuous monitoring of heartbeat and/or heart rate is also possible by means of additional devices (e.g.: wearable devices) added to the system and placed in tight contact with the patient's body. Having an additional device in contact to the patient and connected to the machine in order to transmit data, brings the following drawbacks:

user discomfort due to the added device (wearable or not),
reliability issue due to the tight connection to the patient body,
need of additional connectivity device to machine and vice-versa, which brings further costs of development and updating in existing machines.

WO2011/080194 discloses an apparatus for extracorporeal blood treatment configured to monitor the fluid flow rate of a cardiovascular system of a patient. The apparatus comprises an extracorporeal blood circuit and a connection for connecting the extracorporeal blood circuit to the cardiovascular system. A monitoring device obtains a time-dependent measurement signal from a venous pressure sensor in the blood circuit. The pressure sensor is arranged to detect the pulses originating from the patient heart, wherein the system further comprises a signal processor to process the measurement signal and obtain a pulse profile which is a temporal signal profile of the subject pulse, and to calculate a fluid flow rate based on the temporal signal profile after filtering out the blood pump pressure peaks/pulses.

US2018/078212 discloses a system and method for evaluating the respiratory health of a patient and indicating and characterizing respiratory stress. The device includes a sensor in communication with a patient for generating a biological signal, having a waveform curve in the time domain. The biological signal is processed and a waveform curve is computed, reflective of the respiration rate of the patient. A correlation is then determined between the biological signal waveform curve and respiration rate waveform curve and a respective correlation coefficient is determined. Frequency analysis is performed on the biological signal and a determination is made of a respiration metric reflective of the ratio of spectral components associated with the respiration component of the biological signal in relation to the total spectral components for the biological signal. The correlation coefficient and the respiration metric are combined to form a respiratory stress metric for displaying to a user.

WO2018/112354 discloses a system and method for monitoring and determining patient parameters from sensed venous waveform. This document discloses evaluation of a plurality of frequencies associated with the local maxima of the frequency-domain peripheral venous pressure (PVP) signal, including heart rate frequency (F1) and harmonic frequency (FH) at a harmonic of the heart rate frequency.

Despite of the type of the known sensing technique used for the detection, pump peaks in pressure or flow greatly affect the reliability of reading of the heart beat and/or heart rate.

It is noteworthy that this background section is only for setting out some of the technical challenges faced. The arrangements discussed above should not be construed as being part of the state of the art simply because they are discussed in this section. Conversely, some aspects of the above description may for example not have been made available to the public and should therefore not be construed as such.

The Applicant has therefore identified the need of a sensor and of a sensing technique which are aimed to solve the aforementioned drawbacks.

SUMMARY

For solving the aforementioned drawbacks the Applicant has provided a sensor as disclosed in the present disclosure; the following aspects, which may be combined together and with other parts of the description or claims, will highlight the most relevant technical features of the disclosure.

A $1^{st}$ aspect concerns a non-invasive heartbeat sensor (100) for determining a heartbeat and/or heart rate in an extracorporeal segment (101) of a conduit to be connected to an extracorporeal blood treatment apparatus, said sensor (100) comprising:
  at least one source (53) for directing an optical signal towards the blood flowing in the segment (101), the optical signal being directed along at least one emission axis (54);
  at least one detector (57) for receiving an optical informative signal comprising the signal emitted by said source (53) after passing at least partially the blood flowing in the segment (101), said at least one detector (57) emitting respective output signal (200R) related to the received informative signal,
  a controller (65) configured for receiving the respective output signal (200R) from the at least one detector (57) and for retrieving a heartbeat frequency ($f_{HR}$) and/or detecting a heart rate value, based on the output signal (200R).

Optionally said informative signal is altered by a flow perturbation of the blood flowing in the segment (101), said flow perturbation being at least partially generated by the flow impulses originated by a beating heart.

In $2^{nd}$ aspect according to the $1^{st}$ aspect, wherein the informative signal is altered, in particular at least its amplitude, by, and/or is function of, the blood volume variation or hemoglobin concentration change due at least to the flow impulses originated by a beating heart.

In a $3^{rd}$ aspect according to anyone of the previous aspects, wherein:
  said source (53) is an optical signal source,
  said detector (57) is an optical signal detector (57),
  said informative signal and said signal emitted by said source (53) are optical signals.

In a $4^{th}$ aspect according to anyone of the previous aspects, wherein said flow perturbation of the blood flowing in the segment (101), at a given predetermined time, alters at least the amplitude of said informative signal with respect to the amplitude the signal emitted by said source (53) has at the same predetermined time,
  said property of blood is blood volume variation or hemoglobin concentration change or a parameter directly related to blood volume variation or hemoglobin concentration.

In a $5^{th}$ aspect according to any one of the preceding aspects, wherein the source (53) comprises an optic electromagnetic radiation emitter, optionally a single-wavelength or a multiple wavelength emitter, in particular a single-wavelength, optionally multimode and non-coherent, LED or a multiple wavelength LED, or a single-wavelength LASER or SLED or a combination of plurality of single-wavelength LASERs or SLEDs.

In a $6^{th}$ aspect according to any one of the preceding aspects, wherein said source (53) has at least a main radiation lobe emitting along a predetermined emission axis, optionally wherein said predetermined emission axis is towards the segment (101) and the blood flowing in said segment (101).

In a $7^{th}$ aspect according to any one of the preceding two aspects, the sensor comprises an optic fiber having one end coupled with the source (53) and the other end placed to direct the emitted signal towards the blood along at least said predetermined emission axis.

In an $8^{th}$ aspect according to any one of the preceding three aspects, wherein the multiple wavelength emitter comprises a plurality of optical radiation sources with peak wavelengths in the red and infrared bands, in particular wherein at least an illuminating peak wavelength of the source (53) is comprised between 0.7 µm and 1000 µm and more particularly between 1 µm and 350 µm or between 790 nm and 820 nm, for example between 800 nm and 810 nm, and/or in the red region, between 620 nm and 750 nm.

In a $9^{th}$ aspect according to any one of the preceding aspects, wherein said optical radiation source (53) is configured to transmit a composite optical radiation comprising at least a first component of optical radiation centered on a first wavelength $\lambda_1$, or into a first frequency window comprising said first wavelength, and a second component of optical radiation centered on a second wavelength $\lambda_2$, or into a second frequency window comprising said second wavelength, optionally with a third component of optical radiation centered on a third wavelength $\lambda_3$, or into a third frequency window comprising said third wavelength, and with a fourth component of optical radiation centered on a fourth wavelength $\lambda_4$, or into a fourth frequency window comprising said fourth wavelength, optionally wherein said first, second, third and fourth wavelengths differ each other and/or wherein said first, second, third and fourth frequency windows are at least partially not superimposed in frequency.

In a 10$^{th}$ aspect according to any one of the preceding aspects, wherein the sensor is configured to be arranged in correspondence of the segment (101) of conduit of an extracorporeal blood treatment apparatus or configured to be connected to an extracorporeal blood treatment apparatus, the conduit being configured for blood flow during blood treatment with the apparatus.

In an 11$^{th}$ aspect according to any one of the preceding aspects, wherein said detectors are placed at different radial directions with respect to the emission axis of the source (53), or are arranged at different angular degrees with respect to the emission axis of the source (53) to collect reflected signal, scattered signal and/or transmitted signal depending on their respective position, in particular one first detector being placed at about 180° with respect to the emission axis of the source, and/or one second detector being placed at about 90° with respect to the emission axis of the source, and/or one third detector being placed at about 45° with respect to the emission axis of the source, and/or one fourth detector being placed at about 0° with respect to the emission axis of the source.

In a 12$^{th}$ aspect according to any one of the preceding aspects, wherein said source (53) is configured to transmit said optical radiation in a direction transversal, in particular substantially normal, to a main development axis of said segment (101) and wherein the detectors are configured to receive the optical signal emitted by the source (53) along a direction which is transversal, in particular substantially normal, to the main development axis of said segment (101).

In a 13$^{th}$ aspect according to any one of the preceding aspects, wherein said detectors receive direct, reflected or refracted signal along a respective receiving axis, the receiving axes of said detectors and the emission axis of said source (53) being contained in a same plane.

In a 14$^{th}$ aspect according to any one of the preceding aspects, wherein the segment (101) of the extracorporeal blood treatment circuit is a tube portion, said detectors and said source being disposed around said tube portion at different angular degrees around the same cross section, in particular said tube having a substantially circular cross section.

In a 15$^{th}$ aspect according to any one of the preceding aspects, the sensor further comprises a housing (51) having one portion which is substantially counter-shaped to said tube segment (101), the housing (51) being made of two or more pieces defining a through passage (52) which is counter-shaped to the outer shape of the tube segment to house the tube segment (101) inside the through passage (52), each detector (57) including a respective end placed at the counter-shaped portion facing the tube segment (101) in a coupling condition of the housing (51) with the tube segment (101), in particular the source (53) including an end placed at the counter-shaped portion facing the tube in a coupling condition of the housing with the tube segment.

In a 16$^{th}$ aspect according to any one of the preceding aspect, wherein the source (53) includes an optic fiber (59) having one end coupled with the source (53) and the other end fixed to the housing (51), the other end of the optic fiber being placed at the counter-shaped portion and facing the tube segment (101) in a coupling condition of the housing with the tube segment (101); wherein at least one detector (57), and in particular all detectors (57), includes a optic fiber, one end of the optic fiber being arranged in correspondence of the tube segment (101) being fixed to the housing, the end of the optic fiber being placed at the counter-shaped portion and facing the tube segment (101) in a coupling condition of the housing with the tube segment (101).

In a 17$^{th}$ aspect according to any one of the preceding aspects, wherein the housing (51) comprises a coupled configuration wherein it is configured to substantially fasten against the segment (101) with said counter-shaped portion and an uncoupled configuration, wherein it allows the release of said segment (101); said housing (51) comprising at least a first part (51a) defining a first portion of said counter-shaped portion defining the through passage (52), and a second part (51b) defining a second portion of said counter-shaped portion defining the through passage (52), optionally wherein said first part (51a) and said second part (51b) are separable and/or hinged together to realize—when reciprocally connected—said coupled configuration and—when reciprocally at least partially disconnected—said uncoupled configuration.

In a 19$^{th}$ aspect according to any one of the preceding aspects, the sensor further comprises at least a first detector (57; PD1) configured to receive optical radiation at the first wavelength $\lambda_1$, or into a first frequency window comprising said first wavelength, and a second detector (57; PD2) configured to receive optical radiation at the second wavelength $\lambda_2$, or into a second frequency window comprising said second wavelength, optionally further comprising a third detector (57; PD3) configured to receive optical radiation at the third wavelength $\lambda_3$, or into a third frequency window comprising said third wavelength and a fourth detector (57, PD4) configured to receive optical radiation at the fourth wavelength $\lambda_4$, or into a fourth frequency window comprising said fourth wavelength.

In a 20$^{th}$ aspect according to any one of the preceding aspects, the sensor further comprises a circuitry for transimpedance amplification (62) operatively, in particular electrically, connected to the output of said at least one detector (57), circuitry for transimpedance amplification (62) being configured to transform a current-driven signal generated to by said detector (57) to a voltage-driven output signal.

In a 21$^{st}$ aspect according to any one of the preceding aspects, the sensor further comprises at least one analog-to-digital converting unit (64) whose input is connected operatively, in particular electrically, at least at said output of said detector (57), said analog-to-digital converting unit (64) comprising an output configured to provide a numeric-domain output signal to said controller (65).

In a 22$^{nd}$ aspect according to any one of the preceding two aspects, wherein said analog-to-digital converting unit (64) is provided downstream said circuitry for transimpedance amplification (62).

In a 23$^{rd}$ aspect according to any one of the preceding aspects, the sensor further comprises a low-pass filtering stage 63 operatively coupled to the detector (57), optionally electrically connected to the detector (57), optionally configured to limit the upper band of the output signal (200R) provided by said detector (57) at a frequency lower than 30 Hz, or lower than 10 Hz, or below 9 Hz, or below 8 Hz, or below 7 Hz, or below 6 Hz, or below 5 Hz, or below 4 Hz.

In a 24$^{th}$ aspect according to any one of the preceding two aspects, wherein said low-pass filtering stage (63) is arranged downstream said circuit for transimpedance amplification (62), optionally upstream said analog-to-digital converting unit (64).

In a 25$^{th}$ aspect according to any one of the preceding aspects, wherein said controller (65) is configured for:
electronically calculating a transformation of at least a reference part (200W) of the output signal (200R) from the time domain towards the frequencies domain, obtaining an informative signal spectrum or an output signal spectrum corresponding to the informative signal spectrum,
determining if at least one pump (11) is forcing fluid circulation into said segment (101),
in case the at least one pump (11) is forcing fluid circulation into said segment (101), identifying, and optionally discarding, a first peak of amplitude in said informative signal spectrum or output signal spectrum, said first peak of amplitude, optionally corresponding to a first noise peak of amplitude, corresponding to a spurious flow perturbation in said segment (101) being originated by at least one pump (11) forcing fluid circulation into said segment (101),
performing an electronic identification and subsequent selection of a first sought peak of amplitude in said informative signal spectrum or output signal spectrum, particularly after said discarding has took place, said selection being electronically calculated through an identification of a second sought peak of amplitude in the informative signal spectrum or in the output signal spectrum, the second peak corresponding to a subsequent, particularly a 2$^{nd}$, harmonic of said first sought peak of amplitude,
electronically assigning to at least one provisional heartbeat and/or the heart rate frequency ($f_{HR}$) the frequency corresponding to the first sought peak of amplitude.

In a 26$^{th}$ aspect according to any one of the preceding aspects, wherein said controller (65) is further configured for electronically loading frequency values corresponding to a first lower frequency region (200L) and to at least a second upper frequency region (200U), the second upper frequency region (200U) laying above said first lower frequency region (200L); the electronically processing of the output signal comprising performing the following processing on the informative signal spectrum or output signal spectrum:
filtering out the portion of said informative signal spectrum or output signal spectrum corresponding to the first lower frequency region (200L), or
discarding any peak of amplitude lying in said first lower frequency region (200L), so that the identification, and optionally discarding, of the first noise peak of amplitude and the electronic selection of the first sought peak of amplitude is performed in said at least second upper frequency region (200U).

In a 27$^{th}$ aspect according to any one of the preceding two aspects, wherein the controller (65) is configured for electronically storing and setting an upper frequency value of said lower frequency region (200L) below a frequency threshold for non-physiological cardiac pulses, in particular below 0.4 Hz, or below 0.5 Hz, or below 0.6 Hz, or below 0.7 Hz.

In a 28$^{th}$ aspect according to any one of the preceding aspects, wherein:
the sensor comprises at least one electronic memory operatively accessible to the controller (65), or the sensor is operatively connected to a memory accessible to the controller (65).

In a 29th aspect according to any one of the preceding two aspects, wherein said memory is configured to store at least said upper frequency value of said lower frequency region (200L) and/or said frequency threshold.

In a 30$^{th}$ aspect according to any one of the preceding aspects, when depending on aspect 25, wherein said controller is configured for electronically storing and setting a lowest frequency value of said upper frequency region (200U) corresponding to or upper than the upper frequency value of said lower frequency region (200L).

In a 31$^{st}$ aspect according to anyone of the preceding aspects, when depending on aspect 25, wherein said electronic processing of said output signal comprises low-pass filtering through a filter stage (63) the output signal at a predetermined frequency, optionally below 10 Hz, or below 9 Hz, or below 8 Hz, or below 7 Hz, or below 6 Hz, or below 5 Hz, or below 4 Hz.

In a 32$^{nd}$ aspect according to the preceding aspect, wherein the low-pass filtering is performed before electronically calculating the transformation of the at least the reference part of the output signal from the time domain towards the frequency domain.

In a 33$^{rd}$ aspect according to any one of the preceding aspects, when depending on aspect 25, wherein the identification of a second sought peak of amplitude (200P) is performed by searching a peak of amplitude in the informative signal spectrum or in the output signal spectrum corresponding at a frequency ($f_{HR2}$) corresponding to the double of the frequency ($f_{HR}$) of the first sought peak of amplitude.

In a 34$^{th}$ aspect according to any one of the preceding aspects, when depending on aspect 25, wherein said controller (65), in electronically processing the output signal of said at least one optical detector (57), is configured to perform an electronic selection of a reference window of output signal sampling is performed, said reference window having a predetermined length, optionally less than 1 minute long, or less than 45 seconds long, or less than 30 seconds long, or less than 20 seconds long, or less than 15 seconds long, or less than 10 seconds long, wherein the portion of the output signal constitutes the reference part of the output signal, and wherein the electronic calculation of the transformation of the at least part of the output signal is performed on said reference part of the output signal and is performed after said windowing.

In a 35$^{th}$ aspect according to the preceding aspects, when depending on aspect 25, wherein said identification of the first noise peak of amplitude and/or the identification of the first sought peak of amplitude and/or of said second sought peak of amplitude are performed through an application of a peak detection algorithm on at least part of said informative signal spectrum or output signal spectrum.

In a 36$^{th}$ aspect according to any one of the preceding aspects, when depending on aspect 25, wherein the peak detection algorithm comprises considering a part of the informative signal spectrum or output signal spectrum, said part optionally corresponding to the second upper frequency region (200U), and electronically calculating the derivative of said spectrum obtaining a derivative spectrum, and then comprises a subsequent electronic search and selection of at least one frequency wherein said derivative spectrum changes sign, optionally wherein said derivative spectrum changes sign from a positive value to a negative value proceeding in increasing the frequency of analysis, for identifying positive peaks, the frequency at which said derivative spectrum changes sign from a positive value to a negative value corresponding to said peak.

In a 37$^{th}$ aspect according the any one of preceding aspects, when depending on aspect 25, wherein the peak detection algorithm which the controller (65) is configured to run comprises searching for local relative maximum amplitude points in said informative signal spectrum or output signal spectrum, said part optionally corresponding to the second upper frequency region (200U) by using a moving window signal processing on said spectrum, and a further selection of frequencies corresponding to said maximum amplitude points as a frequency at which a peak occurs.

In a 38$^{th}$ aspect according the any one of preceding aspects, wherein the peak detection algorithm comprises defining a moving window of a predetermined amplitude within at least a part of the informative signal spectrum or output signal spectrum, said part optionally corresponding to the second upper frequency region (200U), and electronically defining at least one, particularly a plurality of, position(s) for said moving window within said at least a part of the informative signal spectrum or output signal spectrum, and for said position(s), optionally for each of said positions, electronically calculating the maximum amplitude of the spectrum within said window, and electronically extracting and storing the frequency corresponding to said maximum amplitude.

In a 39$^{th}$ aspect according to any one of the preceding aspects, when depending on aspect 11, wherein the controller (65) is configured to electronic processing of the output signals of a plurality of the first, second, third, fourth optical detectors (57) performing an electronic averaging, and/or filtering, of the signals of at least part of said optical detectors (57), optionally of all the optical detectors (57), for obtaining a combined output signal in the time domain, and wherein the transformation of the at least the reference part of the output signal from the time domain towards the frequencies domain is performed on said combined output signal,
wherein said output signals of the first, second, third, fourth optical detectors (57) is the result of a reception of at least part of the informative signal through the first, the second, the third and the fourth optical detector (57).

In a 40$^{th}$ aspect according to any one of the preceding aspects, wherein the controller (65) is configured to process the output signal of said at least one optical detector (57) with a pump-associated signal (300P) whose shape is cyclic and/or repeated in time, and is correlated to the pump cycle point, so that to obtain a result signal (301) whose spectrum sees an enhancement of the components or of the peaks relating to the heartbeat or to the heart rate with respect to the components or the peaks associated to the operation a pump (11) of said apparatus.

In a 41$^{st}$ aspect according to the preceding aspect, wherein the controller (65) is configured to process the output signal of said at least one optical detector (57) with said pump-associated signal (300P) so that to render a result signal (301) produced in output of said processing zeroed, in particular periodically or cyclically zeroed, in correspondence to portions of times wherein said pump provides pulses in at least said segment (101).

In a 42$^{nd}$ aspect according to any one of the preceding aspects 40 and 41, wherein the controller (65) is further configured for electronically calculating the average magnitude ($V_m$) of said result signal (301) across a predetermined time length window of analysis, and further comprising a subsequent subtraction of said average magnitude ($V_m$) to at least a portion of said result signal (301), in particular a portion wherein said result signal (301) was not zeroed due to said multiplication, thus producing an averaged signal (301A) constituting the reference part of said output signal to which at least the transformation from the time domain to the frequencies domain is performed.

In a 43$^{rd}$ aspect according to any one of the preceding aspects from 40 to 42, wherein said controller (65) is configured for selecting a plurality of reference parts (200W) of the output signal (200R) by electronically selecting through a sampling window a plurality of portions of said output signal (200R) which are at least partially, optionally fully, not overlapped in time,
performing a transformation from the time domain towards the frequencies domain, obtaining a plurality of informative signal spectrums or a plurality of output signal spectrums corresponding to, or related to, the corresponding plurality of informative signal spectrums, for each of said plurality of reference parts (200W) of the output signal (200R);
for each payload spectrum or output signal spectrum of said plurality:
identifying and discarding a first noise peak of amplitude in said informative signal spectrum or output signal spectrum, said first predetermined peak of amplitude corresponding to or being associated at least partially to an spurious flow perturbation in said segment (101) being originated by at least one pump (11) forcing fluid circulation into at least said segment (101),
performing an electronic identification and subsequent selection of a first sought peak of amplitude in said informative signal spectrum or output signal spectrum after said discarding has took place, said selection being electronically calculated through an identification of a second sought peak of amplitude in the informative signal spectrum or in the output signal spectrum, the second peak corresponding to a 2nd harmonics of said first sought peak of amplitude,
electronically assigning to a provisional heartbeat and/or the heart rate frequency ($f_{HR1}$, $f_{HR2}$, $f_{HR3}$) the frequency corresponding to the first sought peak of amplitude;
calculating a definitive heartbeat and/or heart rate frequency ($f_{HR}$) according to the plurality of provisional heartbeat and/or heart rate frequency values ($f_{HR1}$, $f_{HR2}$, $f_{HR3}$) obtained for each of said spectrum.

In a 44$^{th}$ aspect according to any one of the preceding aspects, wherein according to the previous claim, wherein the definitive heartbeat and/or heart rate frequency ($f_{HR}$) is calculated in accordance to an average calculation among the plurality of provisional heartbeat and/or heart rate frequency values ($f_{HR1}$, $f_{HR2}$, $f_{HR3}$) obtained for each of said spectrum.

In a 45$^{th}$ aspect according to any one of the preceding aspects, wherein said controller (65) is housed into the body of said sensor (100).

In a 46$^{th}$ aspect according to any one of the preceding aspects, wherein said controller (65) is configured to activate an alarm signal in case said controller (65) does not retrieve any heartbeat frequency (f$_{HR}$) and/or does not detect any heart rate value, and or in case said controller (65) after having retrieved at least temporarily said heartbeat frequency (f$_{HR}$) and/or does not detect any heart rate value from said informative signal, in a subsequent time does not retrieve any heartbeat frequency (f$_{HR}$) and/or does not detect any heart rate value, while in presence of said informative signal.

In a 47a aspect a method is disclosed for retrieving heartbeat and/or heart rate in a segment (101) of conduit, said method being performed through a non-invasive optical sensor (100); said method being characterized in that it comprises:

transmitting an optical radiation signal through said segment (101) so that at least part of said optical radiation passes through a portion of liquid, in particular comprising blood, present within said segment (101), the transmission being performed by an optical radiation source (53);

receiving an informative signal through at least one optical detector (57) arranged in substantial correspondence of said segment (101), said informative signal comprising an altered version of said optical radiation signal resulting by said optical radiation signal having at least partially passed the blood present in the segment (101) and/or a portion of the segment (101) itself, wherein said informative signal is altered by, and/or is related to, or is function of, a flow perturbation of the blood flowing in the segment (101), said flow perturbation being at least partially generated by the flow impulses originated by a beating heart, electronically processing an output signal (200R) of said at least one optical detector (57) as a result of detection of at least part of said informative signal by:

electronically calculating a transformation of at least a reference part (200W) of the output signal (200R) from the time domain towards the frequencies domain, obtaining an informative signal spectrum or an output signal spectrum corresponding to, or related to, the informative signal spectrum, determining if at least one pump (11) is forcing fluid circulation into said segment (101), in case the at least one pump (11) is forcing fluid circulation into said segment (101), identifying, and optionally discarding, a first peak of amplitude (f$_{p1}$) in said informative signal spectrum or output signal spectrum, said first peak of amplitude (f$_{p1}$), optionally corresponding to a first noise peak of amplitude, corresponding to or being associated at least partially to a spurious flow perturbation in said segment (101) being originated by the at least one pump (11) forcing fluid circulation into at least said segment (101), performing an electronic search or identification and subsequent selection of a first sought peak of amplitude in said informative signal spectrum or output signal spectrum after said discarding has took place, said selection being electronically calculated through an identification of a second sought peak of amplitude in the informative signal spectrum or in the output signal spectrum, the second peak corresponding to a 2nd harmonics of said first sought peak of amplitude, electronically assigning to at least a provisional heartbeat and/or the heart rate frequency (f$_{HR}$) the frequency corresponding to the first sought peak of amplitude.

In a further aspect 47b a method is disclosed for retrieving heartbeat and/or heart rate in a segment (101) of conduit, said method being performed through a non-invasive optical sensor (100); said method being characterized in that it comprises:

receiving an informative signal through at least one optical detector (57) arranged in substantial correspondence of said segment (101), said informative signal comprising an altered version an optical radiation signal having at least partially passed the blood present in the segment (101), wherein said informative signal is altered by, and/or is related to, or is function of, a flow perturbation of the blood flowing in the segment (101), said flow perturbation being at least partially generated by the flow impulses originated by a beating heart, electronically processing an output signal (200R) of said at least one optical detector (57) as a result of detection of at least part of said informative signal by:

electronically calculating a transformation of at least a reference part (200W) of the output signal (200R) from the time domain towards the frequencies domain, obtaining an informative signal spectrum or an output signal spectrum corresponding to, or related to, the informative signal spectrum, determining if at least one pump (11) is forcing fluid circulation into said segment (101), in case the at least one pump (11) is forcing fluid circulation into said segment (101), identifying, and optionally discarding, a first peak of amplitude (f$_{p1}$) in said informative signal spectrum or output signal spectrum, said first peak of amplitude (f$_{p1}$), optionally corresponding to a first noise peak of amplitude, corresponding to or being associated at least partially to a spurious flow perturbation in said segment (101) being originated by the at least one pump (11) forcing fluid circulation into at least said segment, performing an electronic search or identification and subsequent selection of a first sought peak of amplitude in said informative signal spectrum or output signal spectrum after said discarding has took place, said selection being electronically calculated through an identification of a second sought peak of amplitude in the informative signal spectrum or in the output signal spectrum, the second peak corresponding to a 2nd harmonics of said first sought peak of amplitude, electronically assigning to at least a provisional heartbeat and/or the heart rate frequency (f$_{HR}$) the frequency corresponding to the first sought peak of amplitude.

In a 48$^{th}$ aspect according to the preceding aspects 47a or 47b, the method further comprises a step of electronically loading frequency values corresponding to a first lower frequency region (200L) and to at least a second upper frequency region (200U), the second upper frequency region (200U) laying above said first lower frequency region (200L);

the electronically processing of the output signal comprising performing the following processing on the informative signal spectrum or output signal spectrum:
filtering out the portion of said informative signal spectrum or output signal spectrum corresponding to the first lower frequency region (200L) or
discarding any peak of amplitude lying in said first lower frequency region (200L), so that the identification and discarding of the first noise peak of amplitude ($f_{p1}$) and the electronic selection of the first sought peak of amplitude is performed in said at least second upper frequency region (200U).

In a 49$^{th}$ aspect according to any one of the preceding aspects 47a, 47b and 48, the method comprises electronically storing and setting an upper frequency value of said lower frequency region (200L) below a frequency threshold for non-physiological cardiac pulses, in particular below 0.4 Hz, or below 0.5 Hz, or in particular below 0.6 Hz, or below 0.7 Hz.

In a 50$^{th}$ aspect according to any one of the preceding aspects 47-49, the method further comprises electronically storing and setting a lowest frequency value of said upper frequency region (200U) corresponding to or upper than the upper frequency value of said lower frequency region (200L).

In a 51$^{st}$ aspect according to any one of the preceding aspects 47-50, wherein said electronic processing of said output signal comprises low-pass filtering through a filter stage (63) the output signal at a predetermined frequency, optionally below 10 Hz, or below 9 Hz, or below 8 Hz, or below 7 Hz, or below 6 Hz, or below 5 Hz, or below 4 Hz.

In a 52$^{nd}$ aspect according to the preceding aspect, wherein the low-pass filtering is performed before electronically calculating the transformation of the at least the reference part of the output signal from the time domain towards the frequency domain.

In a 53$^{rd}$ aspect according to any one of the preceding aspects 47-52, the method further comprises providing and/or arranging said non-invasive optical sensor (100) in correspondence of said segment (101) in such a way no part of the sensor gets into contact with any fluid or blood flowing into said segment (101) and in such a way any part of said sensor (100) is introduced into an inner cavity of said segment (101).

In a 54$^{th}$ aspect according to any one of the preceding aspects 47-53, wherein the identification of a second sought peak of amplitude (200P) is performed by searching a peak of amplitude in the informative signal spectrum or in the output signal spectrum corresponding at a frequency ($f_{HR2}$) corresponding to the double of the frequency ($f_{HR}$) of the first sought peak of amplitude.

In a 55$^{th}$ aspect according to any one of the preceding aspects 47-54, the method further comprises a step of loading an electronically preset a threshold (200T) of amplitude, and a subsequent electronic application of said threshold (200T) to the informative signal spectrum or to the output signal spectrum so that identification and discarding of the first noise peak of amplitude and the electronic selection of the first sought peak of amplitude is performed is performed only among those peaks whose amplitude exceeds the threshold (200T).

In a 56$^{th}$ aspect according to any one of the preceding two aspects, wherein the identification of a second sought peak of amplitude (200P) is performed by searching, in the informative signal spectrum or in the output signal spectrum, among the peaks of amplitude having a magnitude exceeding said threshold (200T) and searching among the peaks of amplitude below said threshold (200T).

In a 57$^{th}$ aspect according to any one of the preceding aspects 47-56, wherein in electronically processing the output signal of said at least one optical detector (57) comprises an electronic selection of a reference window of output signal sampling is performed, said reference window having a predetermined length, optionally less than 1 minute long, or less than 45 seconds long, or less than 30 seconds long, or less than 20 seconds long, or less than 15 seconds long, or less than 10 seconds long, wherein the portion of the output signal constitutes the reference part of the output signal, and wherein the electronic calculation of the transformation of the at least part of the output signal is performed on said reference part of the output signal and is performed after said windowing.

In a 58$^{th}$ aspect according to any one of the preceding aspects 47-57, wherein said identification of the first noise peak of amplitude and/or the identification of the first sought peak of amplitude and/or of said second sought peak of amplitude are performed through an application of a peak detection algorithm on at least part of said informative signal spectrum or output signal spectrum.

In a 59$^{th}$ aspect according to the preceding aspect, wherein the peak detection algorithm comprises considering a part of the informative signal spectrum or output signal spectrum, said part optionally corresponding to the second upper frequency region (200U), and electronically calculating the derivative of said spectrum obtaining a derivative spectrum, and then comprises a subsequent electronic search and selection of at least one frequency wherein said derivative spectrum changes sign, optionally wherein said derivative spectrum changes sign from a positive value to a negative value proceeding in increasing the frequency of analysis, for identifying positive peaks, the frequency at which said derivative spectrum changes sign from a positive value to a negative value corresponding to said peak.

In a 60$^{th}$ aspect according to any one of the preceding aspects 47-59, wherein the peak detection algorithm comprises searching for local relative maximum amplitude points in said informative signal spectrum or output signal spectrum, said part optionally corresponding to the second upper frequency region (200U) by using a moving window signal processing on said spectrum, and a further selection of frequencies corresponding to said maximum amplitude points as a frequency at which a peak occurs.

In a 61$^{st}$ aspect according to any one of the preceding aspects 47-60, wherein the peak detection algorithm comprises defining a moving window of a predetermined amplitude within at least a part of the informative signal spectrum or output signal spectrum, said part optionally corresponding to the second upper frequency region (200U), and electronically defining at least one, particularly a plurality of, position(s) for said moving window within said at least a part of the informative signal spectrum or output signal spectrum, and for said position(s), optionally for each of said positions, electronically calculating the maximum amplitude of the spectrum within said window, and electronically extracting and storing the frequency corresponding to said maximum amplitude.

In a 62$^{nd}$ aspect according to any one of the preceding aspects 47-61, the method comprises arranging the at least one optical detector (57) so that its principal direction of detection is axially aligned with a radiation axis and/or with a main radiation lobe of at least said optical radiation source (53), optionally comprising arranging the optical detector (57) in substantial contact with the outer wall of said segment (101) in a position which is diametrically opposed to the position of the optical radiation source (53).

In a 63$^{rd}$ aspect according to any one of the preceding aspects 47-62, the method further comprises arranging at least a second optical detector (57) in substantial correspondence of said segment (101) so that it lies at a different radial direction, or at a different angular degree, with respect to the radiation axis of the optical radiation source (53) or with respect to the main radiation lobe of the optical radiation source (53), to collect a reflected and/or scattered part of said informative signal.

In a 64$^{th}$ aspect according to any one of the preceding aspects 47-63, wherein said different angular degree and/or said different radial direction has an angle of 0°, ≤45° or ≤90° or ≤180° with respect to the radiation axis of the of optical radiation source (53) or with respect to the main radiation lobe of the optical radiation source (53).

In a 65th aspect according to any one of the preceding aspects 47-64, the method comprises:
arranging a first optical detector (57) in substantial correspondence of said segment (101) so that it lies substantially at 45° with respect to the radiation axis of the optical radiation source (53) or with respect to the main radiation lobe of the optical radiation source (53);
arranging a second optical detector (57) in substantial correspondence of said segment (101) so that it lies substantially at 45° with respect to the radiation axis of the optical radiation source (53) or with respect to the main radiation lobe of the optical radiation source (53);
arranging a third optical detector (57) in substantial correspondence of said segment (101) so that it lies substantially at 90° with respect to the radiation axis of the optical radiation source (53) or with respect to the main radiation lobe of the optical radiation source (53);
arranging a fourth optical detector (57) in substantial correspondence of said segment (101) so that it lies substantially at 180° with respect to the radiation axis of the optical radiation source (53) or with respect to the main radiation lobe of the optical radiation source (53);
receiving at least part of the informative signal through the first, the second, the third and the fourth optical detector (57);
wherein the electronic processing of the output signals of the first, second, third, fourth optical detectors (57) comprises averaging and/or filtering the signals of at least part of said detectors, optionally of all those detectors (57), for obtaining a combined output signal in the time domain, and wherein the transformation of the at least the reference part of the output signal from the time domain towards the frequencies domain is performed on said combined output signal.

In a 66$^{th}$ aspect according to any one of the preceding aspects 47-65, wherein transmitting the optical radiation signal comprises transmitting an optical signal centered on at least one predetermined wavelength, optionally comprised in the infrared region, between 1.4 µm and 1000 µm and more particularly between 5 µm and 350 µm, and/or in the red region, between 620 nm and 750 nm.

In a 67$^{th}$ aspect according to any one of the preceding aspects 47-66, wherein transmitting the optical radiation signal comprises transmitting an optical signal having a plurality of components, optionally a first, second, third, fourth component, each of which is centered on a predetermined wavelength different than the wavelength at which the other components of said plurality are centered, realizing a multi-wavelength optical signal, optionally wherein said wavelength is comprised in the infrared region, between 0.7 µm and 1000 µm and more particularly between 1 µm and 350 µm or between 790 nm and 820 nm, for example between 800 nm and 810 nm, and/or in the red region, between 620 nm and 750 nm.

In a 68$^{th}$ aspect according to any one of the preceding aspects 47-67, wherein receiving the informative signal through said first, second, third and fourth optical detector (57) realizes a spatial and wavelength selective reception wherein:
the first optical detector (57) is centered on at least a first wavelength $\lambda_1$ corresponding to the wavelength at which a first component of the transmitted optical signal is centered;
the second optical detector (57) is centered on at least a second wavelength $\lambda_2$ corresponding to the wavelength at which a second component of the transmitted optical signal is centered;
the third optical detector (57) is centered on at least a third wavelength $\lambda_3$ corresponding to the wavelength at which a third component of the transmitted optical signal is centered;
the fourth optical detector (57) is centered on at least a fourth wavelength $\lambda_4$ corresponding to the wavelength at which a fourth component of the transmitted optical signal is centered.

In a 69$^{th}$ aspect according to any one of the preceding aspects 47-68, the method further comprising processing the output signal of said at least one optical detector (57) with a pump-associated signal (300P) whose shape is cyclic and/or repeated in time, and is correlated to the pump cycle point, so that to obtain a result signal (301) whose spectrum sees an enhancement of the components or of the peaks relating to the heartbeat or to the heart rate with respect to the components or the peaks associated to the operation of a pump (11) of said apparatus.

In a 70$^{th}$ aspect according to the preceding aspect, wherein said processing comprises processing the output signal of said at least one optical detector (57) with said pump-associated signal (300P) so that to render a result signal (301) produced in output of said processing zeroed, in particular periodically or cyclically zeroed, in correspondence to portions of times wherein said pump provides pulses in at least said segment (101).

In a 71$^{st}$ aspect according to any one of the preceding aspects 68-70, wherein the electronic processing of the output signal (200R) of said at least one optical detector (57) comprises the following steps:

multiplying, in the time domain, said output signal of said at least one optical detector (57) with a pump-associated signal (300P) whose shape is cyclic and/or repeated in time, and is correlated to the pump cycle point, said multiplying resulting in the generation of a result signal (301); said pump-associated signal (300P) being periodically or cyclically zeroed, in correspondence to portions of times wherein said pump provides pulses in at least said segment (101), so that also the result signal (301) is zeroed in correspondence to the same portions of times.

In a $72^{nd}$ aspect according to any one of the preceding three aspects, wherein said pump-associated signal (300P) is a square wave having a predetermined value in correspondence of the instants of time wherein said pump does not provide pulses in at least said segment (101), and which is zeroed in correspondence to portions of times wherein said pump provides pulses in at least said segment (101).

In a $73^{rd}$ aspect according to any one of the preceding aspects 68-72, the method further comprises electronically calculating the average magnitude ($V_m$) of said result signal (301) across a predetermined time length window of analysis, and further comprising a subsequent subtraction of said average magnitude ($V_m$) to at least a portion of said result signal (301), in particular a portion wherein said result signal (301) was not zeroed due to said multiplication, thus producing an averaged signal (301A) constituting the reference part of said output signal to which at least the transformation from the time domain to the frequencies domain is performed.

In a $74^{th}$ aspect according to any one of the preceding aspects 47-73, the method comprises:
selecting a plurality of reference parts (200W) of the output signal (200R) by electronically selecting through a sampling window a plurality of portions of said output signal (200R) which are at least partially, optionally fully, not overlapped in time,
performing a transformation from the time domain towards the frequencies domain, obtaining a plurality of informative signal spectrums or a plurality of output signal spectrums corresponding to, or related to, the corresponding plurality of informative signal spectrums, for each of said plurality of reference parts (200W) of the output signal (200R);
for each payload spectrum or output signal spectrum of said plurality:
identifying and discarding a first noise peak of amplitude in said informative signal spectrum or output signal spectrum, said first predetermined peak of amplitude corresponding to or being associated at least partially to an spurious flow perturbation in said segment (101) being originated by at least one pump (11) forcing fluid circulation into at least said segment (101),
performing an electronic identification and subsequent selection of a first sought peak of amplitude in said informative signal spectrum or output signal spectrum after said discarding has took place, said selection being electronically calculated through an identification of a second sought peak of amplitude in the informative signal spectrum or in the output signal spectrum, the second peak corresponding to a 2nd harmonics of said first sought peak of amplitude,
electronically assigning to a provisional heartbeat and/or the heart rate frequency ($f_{HR1}$, $f_{HR2}$, $f_{HR3}$) the frequency corresponding to the first sought peak of amplitude;
calculating a definitive heartbeat and/or heart rate frequency ($f_{HR}$) according to the plurality of provisional heartbeat and/or heart rate frequency values (fHR1, fHR2, fHR3) obtained for each of said spectrum.

In a $75^{th}$ aspect according to the preceding aspect, wherein the definitive heartbeat and/or heart rate frequency ($f_{HR}$) is calculated in accordance to an average calculation among the plurality of provisional heartbeat and/or heart rate frequency values ($f_{HR1}$, $f_{HR2}$, $f_{HR3}$) obtained, for each of said spectrum.

In a $76^{th}$ aspect according to any one of the preceding aspects 47-75, wherein the informative signal is substantially not altered by, and/or is substantially not related to or is substantially not function of, size and/or geometry variations of at least a part of the segment (101) at which said information signal is received, said size and/or geometry variations being the results of said flow perturbation of the blood flowing in the segment (101).

In a $77^{th}$ aspect according to any one of the preceding aspects 47-76, the method further comprises activating an alarm, optionally a visible or an auditive alarm, in case no provisional heartbeat and/or heart rate frequency may be retrieved through said electronic search or identification and subsequent selection of the first sought peak of amplitude in the informative signal, or in case to said first sought peak of amplitude in said informative signal spectrum or in said output signal spectrum is not associated to a second peak corresponding to the second harmonics of said first sought peak of amplitude or in case none among other peaks in said informative signal spectrum or in said output signal spectrum corresponding to said first sought peak of amplitude have a corresponding second peak corresponding to a 2nd harmonics of said first sought peak.

In a $78^{th}$ aspect according to any one of the preceding aspects 47-77, wherein said second sought peak of amplitude is arranged at a frequency substantially corresponding to the double of the frequency at which said first peak is located.

In a $79^{th}$ aspect according to any one of the preceding aspects 47-78, the method further comprises:
a step of electronically calculating a difference between a frequency ($f_{P1}$) of the first peak of amplitude associated at least partially to an spurious flow perturbation in said segment (101) and being originated by at least one pump (11) and said heartbeat and/or the heart rate frequency ($f_{HR}$);
a step of electronically comparing said difference, optionally the absolute value of said difference, to a predetermined difference threshold,
a step of generation of a warning signal, in case said difference, optionally the absolute value of said difference, is below said threshold.

In an $80^{th}$ aspect according to the preceding aspect, the method further comprising a step of adapting the speed of rotation, or the flow rate, of at least the blood pump (11) of an apparatus for blood treatment in accordance to said difference, optionally in accordance to said absolute value of said difference.

In an $81^{st}$ aspect according to the preceding aspect, wherein said adapting causes a distancing of the frequency ($f_{P1}$) of the first peak of amplitude associated at least partially to an spurious flow perturbation in said segment (101) and being originated by the at least one pump (11) from said heartbeat and/or the heart rate frequency ($f_{HR}$).

Any one of the method steps may be performed by the controller 65 of the sensor.

Furthermore any one of the sensor features may be part of the sensor according to the method aspects.

In an 82$^{nd}$ aspect a software program, stored on a non-transitory memory support, is disclosed, comprising software code portions suitable to be loaded and executed on an at least one data processing unit, said software code portions being configured to cause the execution of the steps of the method according to one or more of the preceding aspects 47-81.

In an 83$^{rd}$ aspect a distributed computing environment, comprising a plurality of data processing units, configured to be operatively connected one another; said distributed computing environment being configured to cause the execution of the steps of the method according to one or more of the previous aspects 47-81.

In an 84$^{th}$ aspect an apparatus for extracorporeal blood treatment is disclosed, comprising:
a) a blood pump (11) configured at least to control the flow of blood in a blood circuit (6, 7),
b) a circuit for extracorporeal treatment of blood comprising:
  a filtration unit (2) having a primary chamber (3) and a secondary chamber (4) separated by a semi-permeable membrane (5);
  the blood circuit (6, 7) comprising a blood withdrawal line (6) having a first end connected to an inlet of the primary chamber (3), and a blood return line (7) having a first end connected to an outlet of the primary chamber (3), said blood withdrawal line (6) and said blood return line (7) being designed to be connected to a patient cardiovascular system,
  wherein the blood withdrawal line (6) has a second end provided with an arterial connector (40) and the blood return line (7) has a second end provided with a venous connector (41), said arterial connector (40) and said venous connector (41) being designed to be detachably connected to a vascular access of a patient; and wherein said blood circuit is configured to be interfaced with the blood pump (11) for controlling the flow in the blood circuit (6, 7); and
  the secondary chamber (4) being provided with an outlet for an effluent fluid line (13) and optionally with an inlet for a dialysis fluid line (19); and
c) a sensor according to one or more of the aspects 1-46.

In an 85$^{th}$ aspect according to the preceding apparatus aspect, wherein said blood circuit comprises said segment (101).

In an 86$^{th}$ aspect according to any one of the preceding apparatus aspects, wherein said blood circuit is a disposable blood circuit.

In an 87$^{th}$ aspect according to any one of the preceding apparatus aspects, wherein the disposable circuit further comprises at least one fluid line (15, 21, 25, 42; 42a) connected to the blood circuit (6, 7).

In an 88$^{th}$ aspect according to any one of the preceding apparatus aspects, wherein said segment (101) is made in a material, particularly a medical grade plastic material, which is provided with a predetermined degree of transparency to optical radiations, in particular to infrared and/or visible light radiation.

In an 89$^{th}$ aspect according to any one of the preceding apparatus aspects, wherein said sensor is arranged downstream said blood pump (11), optionally upstream the filtration unit (2).

In a 90$^{th}$ aspect according to any one of the preceding apparatus aspects, wherein said sensor is arranged in a position substantially proximal to said venous connector (41).

In a 91$^{st}$ aspect according to any one of the preceding apparatus aspects, wherein the apparatus further comprises at least a user interface, in particular a graphic user interface, said user interface being configured to allow at least viewing said heartbeat frequency ($f_{HR}$), said apparatus being further configured to transmit an alarm signal, in particular a visible and/or auditive alarm signal, in case said sensor (100) does not detect any heartbeat frequency ($f_{HR}$).

In a 92$^{nd}$ aspect according to any one of the preceding apparatus aspects, wherein the sensor is directly constrained to an external portion of a tube being part of the blood circuit (60).

In a 93$^{rd}$ aspect according to any one of the preceding apparatus aspects, wherein the tube is a flexible and optically transparent tube with circular inner and outer sections, in particular the tube does not include a rigid cuvette in correspondence of the sensor.

In a 94$^{th}$ aspect according to any one of the preceding apparatus aspects, wherein the sensor is configured to be directly constrained to any external portion of a tube being part of the blood circuit (60) having circular inner and outer sections.

In a 95$^{th}$ aspect according to any one of the preceding apparatus aspects, wherein the sensor is directly constrained to a rigid and optically transparent rigid cuvette coupled to the blood circuit to allow blood flow passage, in particular the cuvette defining said conduit.

In a 96$^{th}$ aspect according to any one of the preceding apparatus aspects, wherein no additional sensor on the blood circuit is used to determine the heartbeat frequency ($f_{HR}$) and/or the heart rate value. In particular, the non-invasive heart beat sensor of the present aspects is the exclusive and sole sensor used for determining the heartbeat frequency ($f_{HR}$) and/or the heart rate value.

In a 97$^{th}$ aspect a control unit for an heartbeat sensor, in particular for a non-invasive optical heartbeat sensor suitable to be installed in correspondence of a segment (101) of conduit so that to retrieve heartbeat and/or heart rate from analyzing flow perturbations of blood flowing into said segment (101), is provided, said control unit (65) being configured for causing:
  a transmission of an optical radiation signal through said segment (101) so that at least part of said optical radiation passes through a portion of liquid, in particular comprising blood, present within said segment (101), the transmission being performed by an optical radiation source (53);
  a reception of an informative signal through at least one optical detector (57) arranged in substantial correspondence of said segment (101), said informative signal comprising an altered version of said optical radiation signal resulting by said optical radiation signal having at least partially passed the blood present in the segment (101) and/or a portion of the segment (101) itself, wherein said informative signal is altered by, and/or is related to, or is function of, a flow perturbation of the blood flowing in the segment (101), said flow perturbation being at least partially generated by the flow impulses originated by a beating heart, the control unit (65) being further configured for electronically processing an output signal (200R) of said at least one optical detector (57) as a result of detection of at least part of said informative signal by:

electronically calculating a transformation of at least a reference part (200W) of the output signal (200R) from the time domain towards the frequencies domain, obtaining a informative signal spectrum or an output signal spectrum corresponding to, or related to, the informative signal spectrum, identifying and discarding a first peak of amplitude ($f_{p1}$) in said informative signal spectrum or output signal spectrum, said first peak of amplitude ($f_{p1}$), optionally corresponding to a first noise peak of amplitude, corresponding to or being associated at least partially to a spurious flow perturbation in said segment (101) being originated by at least one pump (11) forcing fluid circulation into at least said segment (101), performing an electronic search or identification and subsequent selection of a first sought peak of amplitude in said informative signal spectrum or output signal spectrum after said discarding has took place, said selection being electronically calculated through an identification of a second sought peak of amplitude in the informative signal spectrum or in the output signal spectrum, the second peak corresponding to a 2nd harmonics of said first sought peak of amplitude, electronically assigning to at least a provisional heartbeat and/or the heart rate frequency ($f_{HR}$) the frequency corresponding to the first sought peak of amplitude.

The sensor according to any the previous aspects may be positioned on any tube segment of the blood circuit to detect the heartbeat frequency ($f_{HR}$) and/or the heart rate value, namely either on the arterial line 6 or on the venous line 7.

Additionally, the sensor may not require any dedicated cuvette or coupling element, but may be positioned around any circular tube portion of the blood circuit.

DESCRIPTION OF THE DRAWINGS

The previous and other relevant technical aspects of the disclosure will be described in the subsequent portion of the present disclosure with the aid of the annexed figures wherein:

FIGS. 1A and 1B show a schematic diagram of embodiments of a blood treatment apparatus which the sensor of the present disclosure may be provided to;

DETAILED DESCRIPTION

The present description first discloses a non-invasive, reusable (i.e. non disposable) heartbeat sensor whose operation exploits optical radiation for detecting flow alterations in a fluid comprising blood flowing into a conduit, in particular a conduit or tube of a blood circuit configured to be installed in an extracorporeal blood treatment apparatus 1.

Definitions

For the purposes of the present disclosure:

as per "non-invasive" shall be designated any means, and in particular a sensor, which does not enter into contact with the body of the user, and in particular is neither configured to be introduced into the body of the user nor enters into contact, in particular in direct contact, with a fluid, specifically the blood, of the user flowing into the segment of conduit for performing the detection for which it is conceived;

as per "flow alterations" shall be intended local variation of flow or density or volume of a fluid, in particular albeit in a non-limiting extent, of blood or fluids containing a significant part of blood;

as per "optical radiation" shall be intended any radiation of electromagnetic field lying within the spectrum of the infrared, or visible, or ultraviolet radiation, i.e. any radiation whose wavelength in vacuum is substantially comprised between 1000 μm (300 GHz, corresponding to the far infrared) and 10 nm (3000 THz, corresponding to the Extreme UV) according to ISO standard 21348;

as per "infrared radiation" shall be intended any radiation whose wavelength in vacuum lies between 0.7 μm and 1000 μm and more particularly between 1 μm and 350 μm or between 790 nm and 820 nm, for example between 800 nm and 810 nm;

as per "visible radiation" shall be intended any radiation whose wavelength in vacuum lies substantially between 400 and 750 nm, and as per "red radiation" shall be intended any radiation whose wavelength in vacuum lies substantially between 620 nm and 750 nm.

As just above disclosed, the sensor according to the present disclosure is configured to be installed in an apparatus 1 for extracorporeal blood treatment which may be configured to realize one or more of the following treatments hemodialysis (HD), hemofiltration with pre-dilution (HF-pre), hemofiltration with post-dilution (HFpost), hemofiltration with both pre-dilution and post-dilution (HFpre-post), hemodiafiltration with pre-dilution (HDFpre), hemodiafiltration with post-dilution (HDFpost), hemodiafiltration with both pre-dilution and post-dilution (HDFpre-post), ultrafiltration (UF) or configured to be installed on a segment 101 of a blood circuit suitable to be installed on said apparatus.

Brief Description of the Apparatus

Figure 1A:
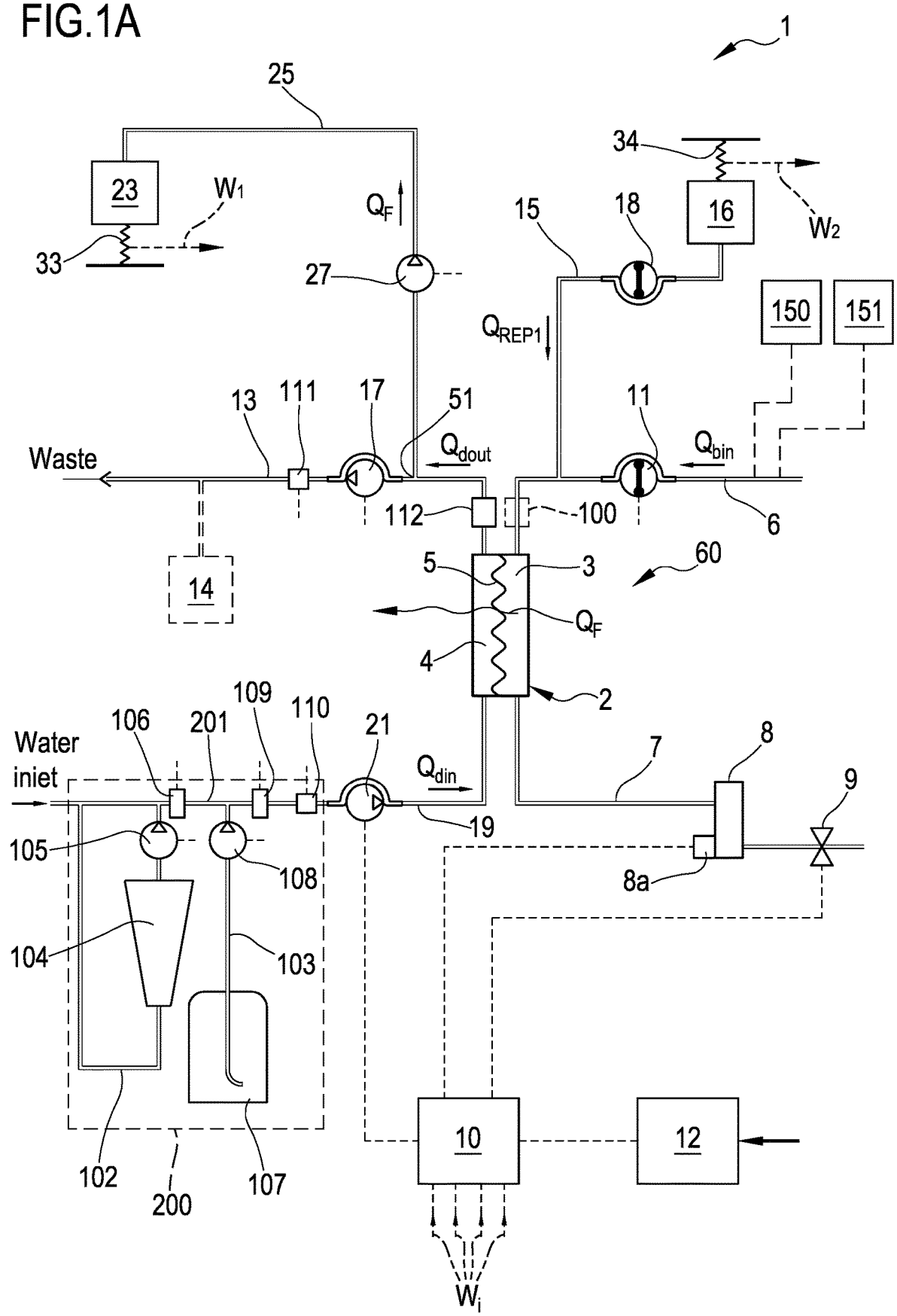
Figure 1B:
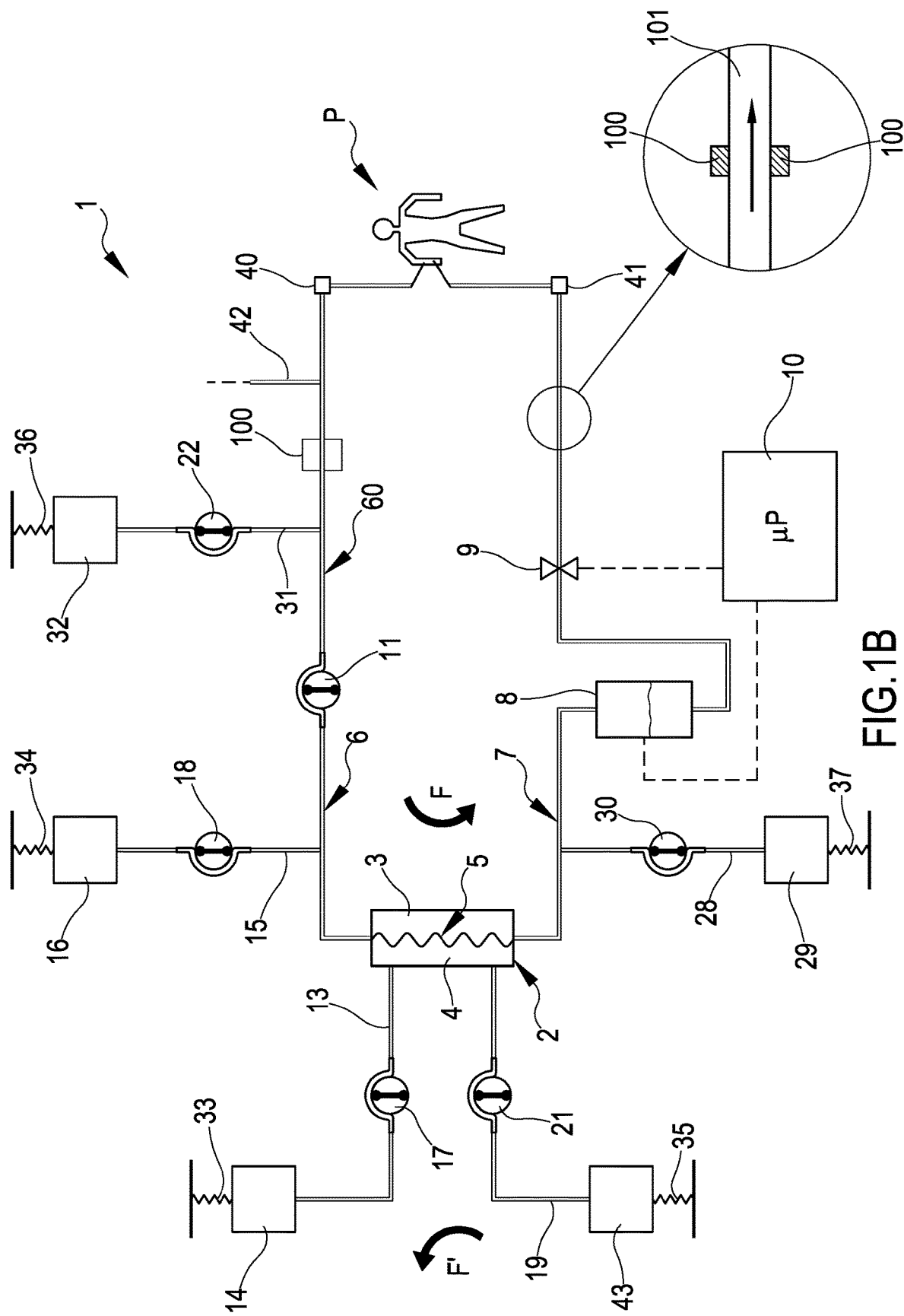

For the purposes of clarity of exposure and contextualization of the operation of the sensor herewith disclosed, a brief description of the apparatus 1 is hereinafter provided. Non-limiting embodiments of an apparatus 1 for extracorporeal treatment of blood—which may implement innovative aspects of the invention—are shown in FIGS. 1A and 1B. In below description and in FIGS. 1A and 1B same components are identified by same reference numerals.

The apparatus 1 includes at least one sensor 100 which may be configured to determine at least the heartbeat and/or the heartrate. As apparent from the following description, sensor 100 may be placed in any position on the hydraulic circuit, and particularly on the blood circuit 60. FIG. 1A shows an apparatus 1 suitable for chronic treatments and FIG. 1B discloses an apparatus 1 suitable for delivering acute treatments; both apparatuses are configured to deliver any one of treatments like ultrafiltration, hemodialysis and hemodiafiltration.

Figure 2:
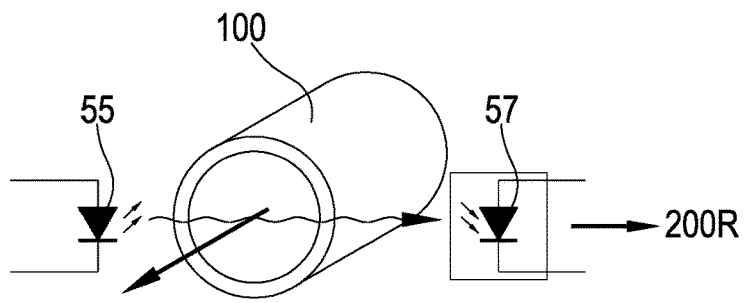
FIG. 2 shows an operation principle of the sensor of the present disclosure.
Figure 12:
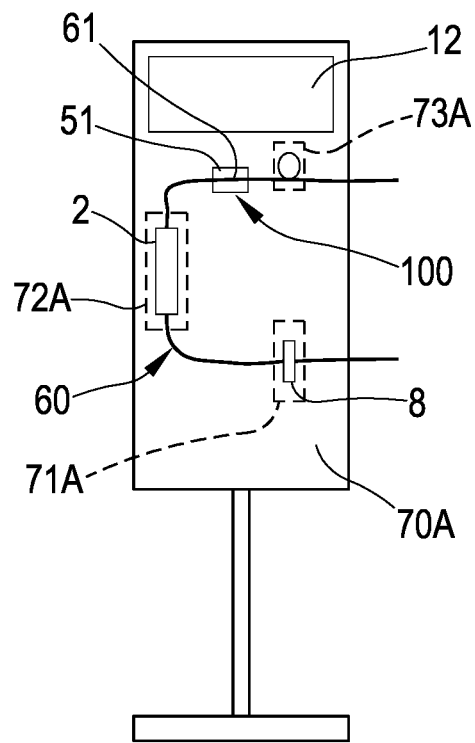
FIG. 12 shows a schematic front view of a cabinet structure for the apparatus of FIG. 1A or 1B.

The apparatus 1 comprises a treatment unit 2 (such as an hemofilter, an ultrafilter, an hemodiafilter, a dialyzer, a plasmafilter and the like) having a primary chamber 3 and a secondary chamber 4 separated by a semipermeable membrane 5; depending upon the treatment, the membrane 5 of the treatment unit 2 may be selected to have different properties and performances. A blood withdrawal line 6 is connected to an inlet of the primary chamber 3, and a blood return line 7 is connected to an outlet of the primary chamber 3. The blood withdrawal line 6, the primary chamber 3, and the blood return line 7 are part of an extracorporeal blood circuit, which is globally identified with reference number 60 in FIGS. 1A and 1B. In use, the blood withdrawal line 6 and the blood return line 7 are connected to a needle or to a catheter or other access device (not shown) which is then placed in fluid communication with the patient vascular system, such that blood may be withdrawn through the blood withdrawal line, flown through the primary chamber and then returned to the patient's vascular system through the blood return line. As marked in FIG. 1B with the curved arrow F, the normal flow of fluid imposed by the blood pump 11 is from the arterial connector 40 to the venous connector 41; thus wording "downstream" and "upstream" will be referred considering such flow. FIG. 1A shows blood flow rate Qbin and its normal flow direction. In a non-limiting solution, the blood withdrawal line 6 and the blood return line 7 are made of transparent plastic material, which allows e.g., to identify fluid flow, presence of bubbles or air therein or even clogs (through dedicated sensors). At least the inner part of the blood withdrawal line and the blood return line, and particularly any part of the disposable circuit herein described are made in a material specifically conceived for medical applications, and in particular in a plastic material which is compatible, and does not releases substances, when getting in contact with body fluids, and/or with lipids—e.g. lipids of pharma drugs or nutrients. Such plastic may be e.g. PVC, in particular high-grade medical PVC. An air separator, such as a bubble trap 8 may be present on the blood return line; the extracorporeal blood circuit is supported by one or more holders provided, in a conventional manner, by the support framework 70a of the apparatus 1. For instance, as shown in FIG. 12, the extracorporeal blood circuit 60 may be supported by a holder 71 holding the bubble trap, by a holder 72 holding the treatment unit 2, and by a holder 73 located in correspondence of the blood pump. A safety clamp 9 controlled by a control unit 10 may be present on the blood return line downstream the bubble trap 8. A bubble sensor 8a, for instance associated to the bubble trap 8 or coupled to a portion of the line 7 between bubble trap 8 and clamp 9 may be present: if present, the bubble sensor is connected to the control unit 10 and sends to the control unit signals for the control unit to cause closure of the clamp 9 in case one or more bubbles above certain safety thresholds are detected. The blood flow through the blood lines may be controlled by a blood pump 11, for instance a peristaltic blood pump, acting either on the blood withdrawal line (as shown in FIG. 1) or on the blood return line. An operator may enter a set value for the blood flow rate Qb: the control unit 10, during treatment, is configured to control the blood pump based on the set blood flow rate. It is noted that the control unit 10 may also be connected to a user interface 12, for instance a graphic user interface, which receives operator's inputs (such as, inter alia, the set value for the blood flow rate) and displays the apparatus outputs. For instance, the graphic user interface 12 may include a touch screen for both displaying outputs and allowing user entries, or a display screen and hard keys for entering user's inputs, or a combination thereof. A spent dialysate line 13 configured for evacuating an effluent fluid coming from the secondary chamber 4 is connected, at one end, to an outlet of the secondary chamber 4 and, at its other end, to a waste which may be a discharge conduit or an effluent fluid container 14 (dashed lines in FIGS. 1 and 2) collecting the fluid extracted from the secondary chamber. An effluent fluid pump 17 operates on the spent dialysate line 13 under the control of control unit 10 to regulate the flow rate $Qd_{out}$ of effluent fluid through the spent dialysate line. The net ultrafiltration (i.e. the net fluid removed from the blood across the semipermeable membrane of the treatment unit 2 may be determined by the flow rate difference between a dialysis fluid pump 21 on the fresh dialysis fluid line 19 and the effluent fluid pump 17. Alternatively (or in combination) the apparatus may also include an ultrafiltration line 25 branching off the spent dialysate line 13 and provided with a respective ultrafiltration pump 27 also controlled by control unit 10 to cause a flow rate $Q_F$ along the ultrafiltration line. The embodiments of FIGS. 1A and 1B present a pre-dilution fluid line 15 connected to the blood withdrawal line: this line 15 supplies replacement fluid from an infusion fluid container 16 connected at one end of the pre-dilution fluid line. Although FIG. 1A shows a container 16 as source of infusion fluid, this should not be interpreted in a limitative manner: indeed, the infusion fluid may alternatively come from an on line preparation section. Note that, alternatively to the pre-dilution fluid line, the apparatus of FIG. 1A may include a post-dilution fluid line (not shown in FIG. 1A) connecting an infusion fluid container or an on line preparation section of infusion solution to the blood return line. Finally, as a further alternative (not shown in FIG. 1A) the apparatus may include both a pre-dilution and a post infusion fluid line: in this case each infusion fluid line may be connected to a respective infusion fluid container or may receive infusion fluid from a same source of infusion fluid such as a same infusion fluid container or an online preparation section. In case the infusion fluid is prepared online, the source of infusion fluid may be an online preparation section part of the apparatus 1 (i.e. as the online preparation section 200 described herein below) or a distinct device analogous to section 200 and connected to the infusion line or lines and configured for supplying fluid to the post and/or pre dilution lines (see FIG. 1A). Furthermore, an infusion pump 18 operates on the infusion line 15 to regulate the flow rate $Q_{rep1}$ through the infusion line 15. Note that in case of two infusion lines (pre-dilution and post-dilution) each infusion line may be provided with a respective infusion pump. The apparatus of FIG. 1A, further includes a fluid preparation line 19 connected at one end with a water inlet and at its other end with the inlet of the secondary chamber 4 of the filtration unit for supplying fresh treatment liquid to the secondary chamber 4. A dialysis fluid pump 21 works on the fluid preparation line under the control of said control unit 10, to supply fluid from a source of fresh treatment liquid (such as a container or the section 200 for online preparing fresh dialysis liquid) to the secondary chamber at a flow rate $Qd_{in}$. In the example of FIG. 1A, the line 19 links the hemodialyzer or hemodiafilter 2 to online preparation section 200, which is configured for preparing the dialysis liquid: section 200 comprises a main line 201, the upstream end of which is designed to be connected to a supply of water. A first secondary line 102 and a second secondary line 103 are connected to the main line 201 and are configured to at least supply the necessary quantity of a buffer and the necessary quantity of electrolytes. The first secondary line 102, which may be looped back onto the main line 201, is configured for fitting a first container 104, such as a bag or cartridge or other container, containing a buffer. Line 102 is furthermore equipped with a first metering pump 105 for dosing the buffer into the fresh treatment liquid: as shown in FIG. 1A the pump may be located downstream of the first container 104. The operation of the pump 105 may be controlled by the control unit 10 based upon the comparison between: 1) a set point value for the buffer concentration of the solution forming at the junction of the main line 201 and the first secondary line 102, and 2) the value of the buffer concentration of this mixture measured by through a first probe 106 located either in the first secondary line downstream the first container 104 or in the main line 201 immediately downstream of the junction between the main line 201 and the first secondary line 102. Furthermore, the free end of the second secondary line 103 is intended to receive fluid from second container 107 containing a concentrated saline solution, e.g. electrolytes such as sodium chloride, calcium chloride, magnesium chloride and potassium chloride. In a variant also the second secondary line 103 may be looped back onto the main line 201. Moreover, it is possible envisaging a plurality of independent second secondary lines 103 in the case one wishes to feed separate electrolytes or electrolyte compositions from respective containers. Note that the second secondary line 103 is equipped with a second metering pump 108 for dosing electrolytes into the fresh treatment liquid; operation of the second metering pump depends on the comparison between 1) a conductivity set-point value or an electrolyte concentration set-point value for the solution forming at the junction of the main line 201 with the second secondary line 103, and 2) the value of the conductivity or electrolyte concentration of this solution measured by through a second probe 109 located either in the second secondary line downstream of second container 107 or in the main line 201 immediately downstream of the junction between the main line 201 and the secondary line 103. Note that the specific nature of the concentrates contained in containers 104 and 107 may be varied depending upon the circumstances and of the type of fresh treatment fluid to be prepared. Moreover, the nature and the position of the first and second probes may depend upon the type of buffer used, the type of electrolyte concentrate(s) adopted and upon the specific configuration of the circuit formed by the main line and the secondary lines. Furthermore, as already mentioned, more than two secondary lines, with respective concentrate containers and respective metering pumps may be in case a plurality of different type of substances need to be added for the preparation of the fresh treatment fluid. The second probe is generally a conductivity meter configured for measuring the dialysis fluid conductivity upstream the filtration unit 2. Of course, dialysis fluid conductivity is set by the operator or set and controlled by the apparatus during treatment. Correspondingly, the apparatus includes a further conductivity meter 112 placed on the spent dialysate line 13 to sense conductivity $\sigma_{out}$ of the dialysis fluid downstream the filtration unit 2. Both conductivity meters 109 and 112 provide the respective measuring signal to the apparatus control unit 10. Flow sensors 110, 111 (either of the volumetric or of the mass type) may be used to measure flow rate in each of the lines. Flow sensors are connected to the control unit 10. In the example of FIG. 1A, where the infusion line 15 and the ultrafiltration line 25 lead to a respective container or bag 16, 23, scales may be used to detect the amount of fluid delivered or collected. For instance, the apparatus of FIG. 1A includes a first scale 33 operative for providing weight information $W_1$ relative to the amount of the fluid collected in the ultrafiltration container 23 and a second scale 34 operative for providing weight information $W_2$ relative to the amount of the fluid supplied from infusion container 16. The embodiment of FIG. 1B shows an alternative apparatus 1 designed for delivering acute treatments like hemodialysis, hemofiltration, hemodiafiltration and ultrafiltration. In the apparatus shown in FIG. 1B the same components described for the embodiment of FIG. 1A are identified by same reference numerals and thus not described again. Differently from the hemodiafiltration apparatus of FIG. 1A, the apparatus of FIG. 1B does not present an on-line fluid preparation since all fluids are prepackaged in sterile containers. Fresh dialysis fluid is contained in a fresh dialysis container 43. Additionally, fluid line 19 and effluent line 13 are of the disposable type and directly and irremovably constrained to the treatment unit 2. Consequently, dialysis pump 21 and effluent pump 17 are peristaltic pumps (and not volumetric pumps as per the embodiment of FIG. 1A). The embodiment of FIG. 1B presents the pre-dilution fluid line 15 connected to the blood withdrawal line 6: this line 15 supplies replacement fluid from the infusion fluid container 16 connected at one end of the pre-dilution fluid line. Furthermore, the apparatus may further comprise the infusion pump 18, which operates on the infusion line 15 to regulate the flow rate Qrep through the infusion line. Note that alternatively or in combination to the pre-dilution fluid line the apparatus may include a post-dilution fluid line 28 connecting an infusion fluid container 29 to the blood return line 7. A further pump 30, for instance a peristaltic pump, may act under the control of control unit 10 on the post-dilution fluid line 28 and thus also be part of means for regulating the flow through the fluid lines. Additionally, the disposable circuit shown in FIG. 1B may present a further infusion line 31 connected, at one end, with the blood withdrawal line 6 positioned upstream the blood pump 11 and, at its other end, with a further infusion fluid container 32, which for instance may contain a drug, or a regional anticoagulant such as a citrate solution. This further infusion line is herein referred to as pre-blood pump pre-dilution infusion line 31. The means for regulating comprises a pbp pump 22, for instance a peristaltic pump controlled by control unit 10, acting on a segment of the pre-blood pump pre-dilution infusion line 31 to regulate a pre-blood pump infusion rate Qpbp. The pump 22 is typically part of the apparatus 1, and therefore is not part of the disposable. Alternatively of in combination with the aforementioned fluid lines, the apparatus of FIG. 1B may comprise one or more auxiliary lines 42, which are connected, at one end, with a blood withdrawal line 6. FIG. 2 shows a single auxiliary line. A further pump, not shown in FIG. 2, for instance a peristaltic pump, may act under the control of control circuit 10 on the auxiliary line and thus also be part of said means for regulating the flow through the fluid lines. In the embodiment of FIG. 1A, the apparatus includes a first scale 33 operative for providing weight information $W_1$ relative to the amount of the fluid collected in the ultrafiltration container 23 and a second scale 34 operative for providing weight information $W_1$ relative to the amount of the fluid collected in the infusion fluid container 16. The scales are all connected to the control unit 10 and provide said weight information $W_i$ for the control unit to determine the actual quantity of fluid in each container as well as the actual flow rate of fluid supplied by or received in each container. FIG. 1B further includes third, fourth and fifth scales 35, 36, 37 to detect weight of respectively the fresh dialysis container 43, citrate infusion container 32 and post infusion fluid container 29. In the example of FIG. 1A, in order to control the fluid balance between the quantity of fluid supplied to the secondary chamber 4 and the quantity of fluid extracted from the secondary chamber, the flow sensors 110, 111 positioned on the fresh dialysate line and on the spent dialysate line 13 provide the control unit 10 with signals indicative of the flow of fluid through the respective lines and the scale or scales provide weight information which allow the control unit to derive the flow rate through the ultrafiltration line 25 and, if present, through the infusion line 15. The control unit is configured to control at least pumps 17, 21 and 27 to make sure that a prefixed patient fluid removal is achieved in the course of a prescribed treatment time, as required by the prescription provided to the control unit, e.g. via user interface 12. Note that other fluid balance systems may be used: for instance in case the apparatus includes a container as source of fresh treatment fluid and a container to collect waste (see FIG. 1B), then scales may be used to detect the amount of fluid delivered or collected by each container and then inform the control unit accordingly. As a further alternative, systems based on volumetric control may be used where the preparation line 19 and the spent dialysate line 13 are connected to a balance chamber system assuring that—at each instant—the quantity of liquid flowing into line 19 is identical to the quantity of fluid exiting from line 13. From a structural point of view one or more, containers 104, 107, 16, 23 may be disposable plastic containers. The blood lines 6, 7 lines and the filtration unit may also be plastic disposable components which may be mounted at the beginning of the treatment session and then disposed of at the end of the treatment session. Pumps, e.g. peristaltic pumps or positive displacement pumps, have been described as means for regulating fluid flow through each of the lines; however, it should be noted that other flow regulating means may alternatively be adopted such as for example valves or combinations of valves and pumps. The scales may comprise piezoelectric sensors, or strain gauges, or spring sensors, or any other type of transducer able to sense forces applied thereon.

Description of the Sensor

The sensor according to the present disclosure exploits the variation of physical properties of an optical radiation for detecting flow alterations in a fluid comprising blood flowing into the segment 101 of a tube or conduit for extracorporeal blood treatment. It derives that the segment 101 shall provide some transparency to the wavelengths of optical radiation involved in the measurement. In particular, the sensor 100 which is object of the present disclosure allows to detect blood and in particular red cells concentration variations over time, through which it is possible to identify a heartbeat and thus an heart rate; more in detail, when radiated by a proper optical radiation, the transmission of the radiation through the blood variates according to its concentration, in particular as a function of the concentration of red cells, which in turn variates in accordance to the peaks of flow produced by the heartbeat. Therefore, counting the cadence of the peaks of flow, i.e. the peaks (or correspondingly reductions) of the radiation transmission, it is possible to detect the heartbeat and therefore the frequency at which the heart beats.

The sensor 100 according the present disclosure is not invasive and allows for a continuous monitoring of the heartbeat that may last without significant interruption for any wanted time, and for the entire blood treatment length as required by the standard or acute therapy the patient is subject to. Since during normal operations no parts of the sensor get in contact with the blood of the user, the sensor which is object of the present disclosure is reusable, and thus does not constitute a so-called disposable device. This way, some processing intelligence may be arranged on board thereof, without involving relevant exchange costs, that would be otherwise present in any case wherein known sensors get in contact with the blood. The sensor 100 is in particular placed onto a segment of the blood circuit, specifically of the blood withdrawal line 6 and/or the blood return line 7. More than one sensor 100 may be used depending on the circumstances and placed in different position along the conduit. In a non-limiting extent, any electronically sensitive part of the circuitry arranged within the body of the sensor shall be properly protected against external agents, in accordance to an appropriate IP standard, so that—should the case may be—the sensor may be washed, or cleaned, or sterilized or sanitized in a convenient way without significant risks of damaging and without contaminating the blood lines when newly installed for subsequent treatments.

In general terms, and according to the schematic representation of FIG. 2, the sensor 100 comprises at least one optic source 55 that emits an optical radiation through the segment 101 of conduit which is filled with fluid comprising blood. The optical radiation traverses thus the walls of the segment 101 of conduit and the fluid therein contained, then reaches an optical sensor 57 which is capable of detecting at least a variation of amplitude of the received optical radiation. The sensor transmits an output signal 200R which is then properly processed to extract the heart rate. In a particular embodiment disclosed in FIG. 3, the sensor 100 comprises a plastic housing 51 only schematically represented in the annexed drawings. The housing 51 is designed to tightly couple to the blood line segment 61 of the extracorporeal blood circuit 60 where the blood or plasma parameters need to be measured. The housing 51 may be a standalone body or may be attached to or be part of a support framework 70a of the apparatus. For instance, the housing 51 may be attached to the front panel of the support framework (see FIG. 12) and configured to receive at least one (in the examples of the drawings only one) segment 61 of the extracorporeal blood circuit. To this aim, the housing 51 may be counter-shaped directly to a portion of a blood line tubing, namely to a circular cross section segment of flexible transparent plastic tubing of a blood withdrawal line 6 or blood return line 7. The housing may be an open-and-close housing defining an inside through passage 52 destined to receive the tube of the blood circuit.

Figure 3:
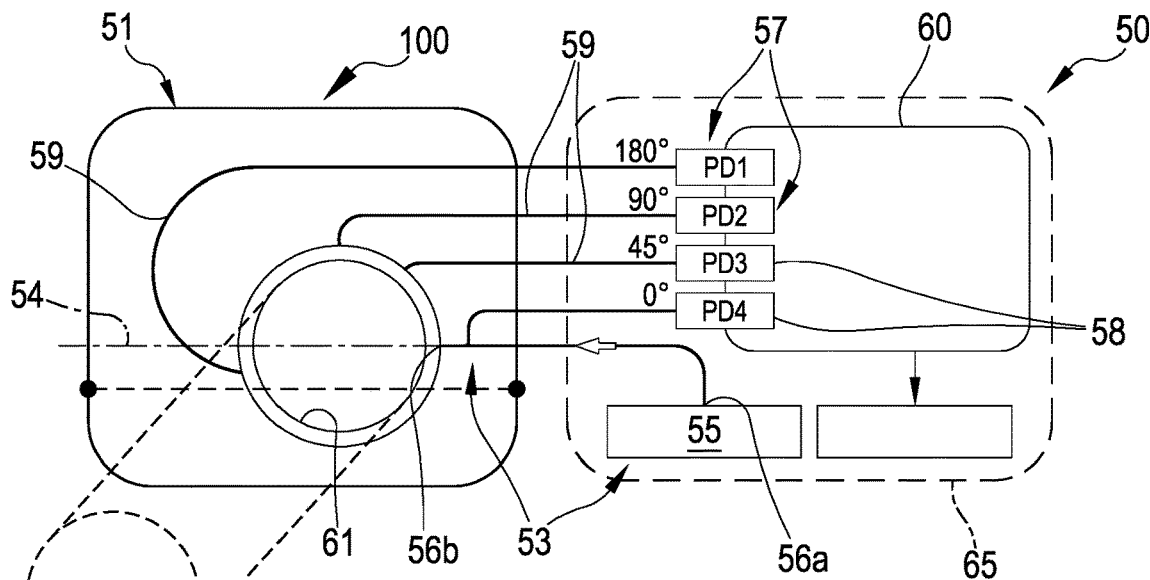
FIG. 3 shows a schematic view of the sensor according to the present disclosure.
Figure 3A:
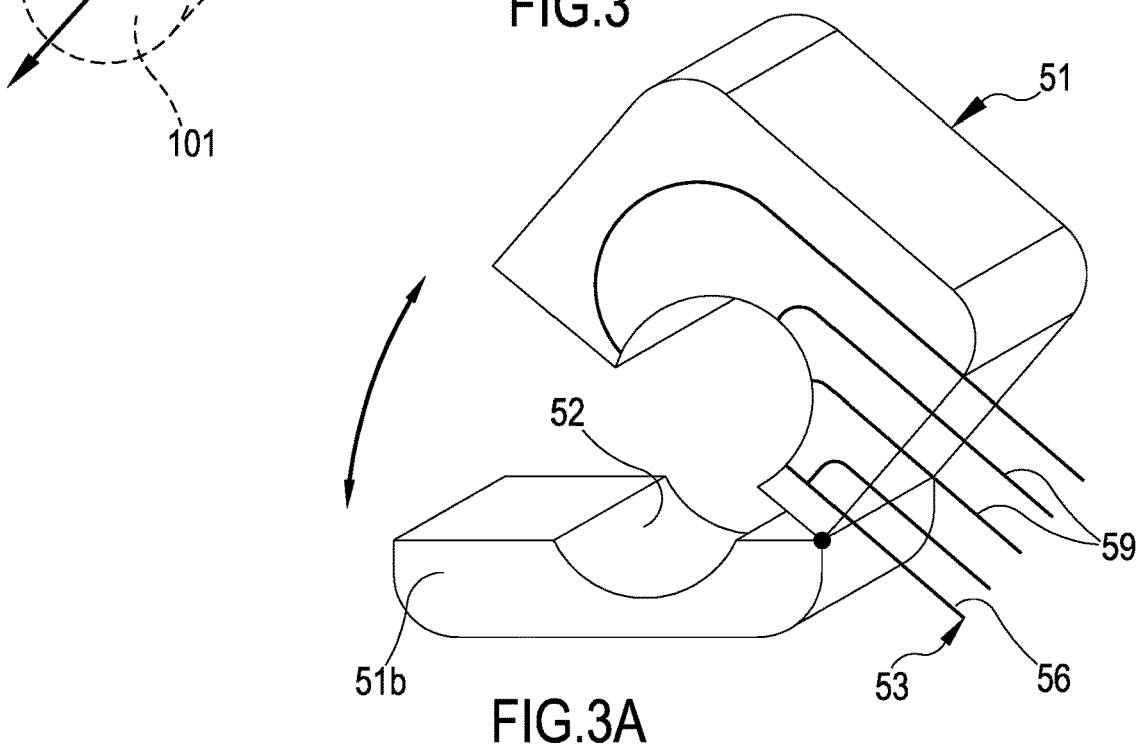
FIG. 3a shows a perspective view of the sensor according to the present disclosure in an operative configuration wherein the body thereof is open for allowing the extraction or introduction of a segment of tube or conduit of a blood circuit into a cavity wherein sensing elements are provided.
Figure 3B:
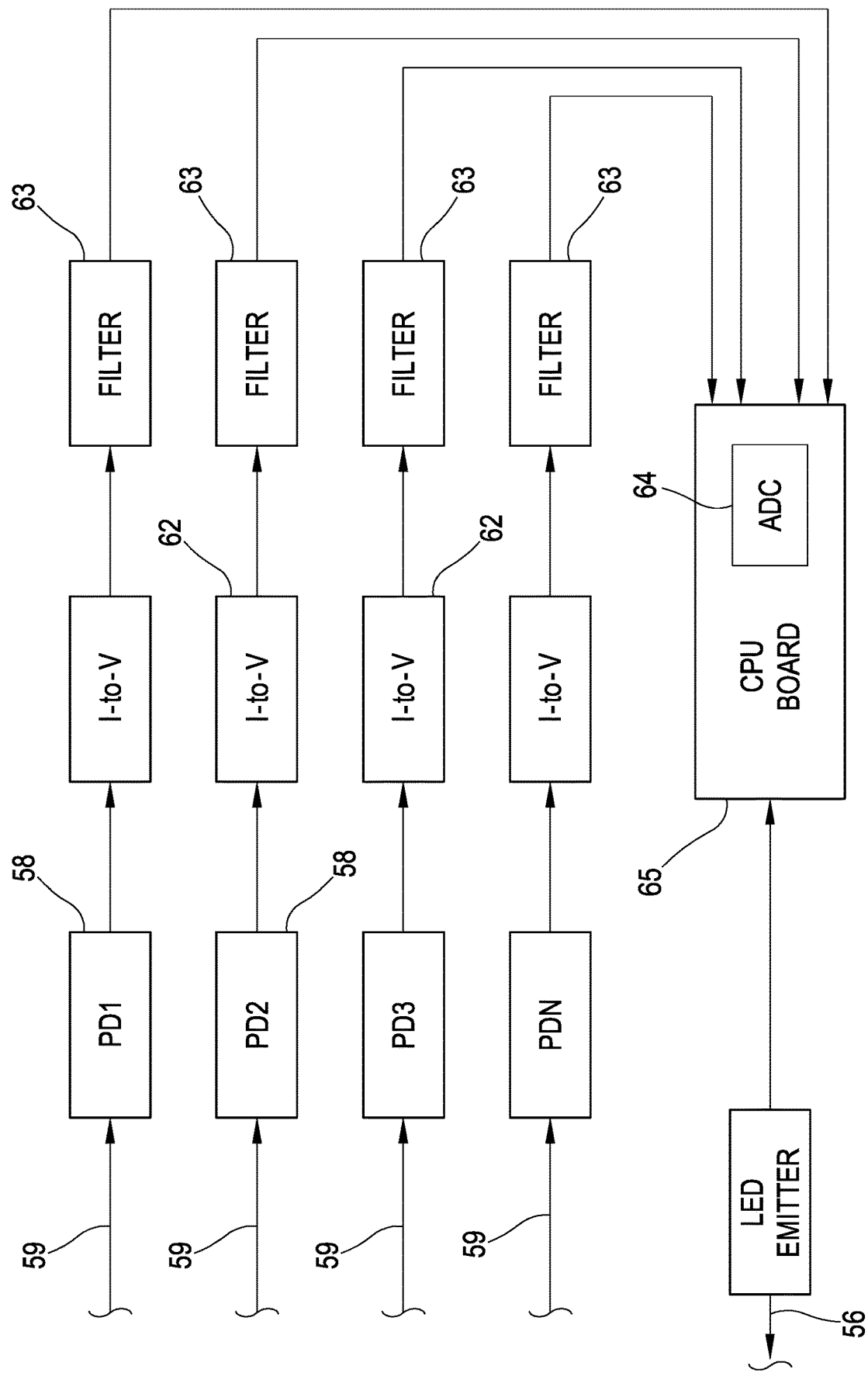
FIG. 3b shows a perspective view of a circuit configuration of a particular embodiment of the sensor according to the present disclosure.

Notably, the housing 51 may be made of two or more parts 51a, 51b either separate or joined, e.g. hinged, together so to define an uncoupled configuration (see FIG. 3a) and a coupled configuration (see FIG. 3). In the coupled configuration the through passage 52 is counter-shaped to the tube to be received so as to perfectly couple with it and receives the tube. It may be noted that the first part 51a defines a first portion of the counter-shaped portion of the through passage 52, while the second part 51b defines a second portion of the counter-shaped portion of the through passage 52: more in detail in the annexed figures those parts are equally-shaped halves of circle. The schematic drawings illustrate a situation where the flexible blood tube is coupled to the sensor 100. However, the housing 51 may be alternatively shaped to couple with a rigid cuvette (such as the cuvette for the Hemoscan® sensor from Baxter). In such a case, the flexible tubing of the blood circuit has the rigid cuvette properly applied so that blood flowing in the extracorporeal blood circuit 60 passes through the cuvette itself; the through passage is in this latter case counter-shaped to the outer surface of the cuvette which is not necessarily rounded but may alternatively have flat outer surfaces (polygonal section).

It is clear that in case the housing is to be applied to the circular flexible tubing of the extracorporeal blood circuit 60, any position of the sensor along the blood withdrawal line 6 or blood return line 7 is suitable. In case the sensor 100 has a through passage counter-shaped to a specific cuvette, the sensor is to be applied in correspondence of the cuvette itself for proper working.

The housing 51 may be made of a high absorption material which prevents external ambient light from reaching the receivers. This helps reducing the risk that outer optical radiation sources negatively influence the reading of the heartbeat providing spurious peaks or reductions of light amplitude, in particular when those peaks or reductions have a frequency lying close to that of a physiological heartbeat.

The sensor 100 comprises at least one signal source 53 for directing a signal towards the blood along an emission axis 54. The signal source 53 may include any suitable signal emitter, such as an optic (or an acoustic) emitter directing a proper emitted signal towards the inside of the tube where blood is flowing. In embodiments of the present invention, the signal source 53 includes an electromagnetic radiation source, particularly a light source such as a LED source, a SLED or a Laser source. In the following description, we refer to an optical emitter and in detail to a LED emitter 55; however, this should not be interpreted as limiting. It has been noted that the non-limiting peak wavelength of the optical radiation transmitted by the signal source 53 is set to 800-810 nm, corresponding to that point of the Hgb absorption spectra where absorption is not dependent on oxygenation. Again, this is not to be considered a limiting aspect; in fact, any optical radiation in the field of the infrared or red light may be in principle used for the present application. In a simple embodiment like that disclosed in FIG. 2, the signal source 53 may comprise a simple multimode, non-coherent, LED which transmits an optical radiation with a first peak wavelength $\lambda_1$ within the infrared or red region, or within a predetermined emission window of wavelengths (or frequencies) wherein said first peak wavelength $\lambda_1$ falls. The specific implementation of the signal source 53 otherwise includes a multiple wavelength LED emitter (namely, MTMD6788594SMT6, Marktech Optoelectronics, NY, USA) used for light emission. The emitter 55 in particular includes 5 LEDs on the same chip, with peak wavelengths $\lambda_1, \lambda_2, \lambda_3, \lambda_4, \lambda_5$, in the red/infrared bands. Those five LEDs emit optical radiation with peak wavelengths which differ one another. This way, wavelength (or equivalently frequency) diversity may be obtained for the purposes of increasing the precision of detection of the heartbeat, and for reducing any external influence on the reading of the heartbeat.

The source 53 further comprises an optic fiber 56 having one end 56a coupled with the signal emitter 55 and the other end 56b fixed to the housing 51 and placed to direct the optical radiation towards the blood along the emission axis 54 of the source 53. As shown in FIG. 3, the second end 56b of the optic fiber 56 is placed at the counter-shaped portion and faces the tube in a coupling condition of the housing with the tube segment 61.

The sensor 100 comprises a plurality of detectors 57 for receiving the signal emitted by said source after at least partially passing through the blood; in particular the detectors 57 collect the reflected signal, the scattered signal and/or the transmitted signal depending on their respective position. Since the emitter 55 is a LED emitter, the detectors 57 may comprise a photodiode receivers 58. In an embodiment, the detectors 57 are placed at different angular degrees with respect to the emission axis 54. In more detail, the sensor 50 of FIG. 3 includes four different detectors 57 for receiving the electromagnetic radiation from the source 53, one first photodiode receiver PD1 being placed at about 180° with respect to the emission axis 54 of the signal source, one second photodiode receiver PD2 being placed at about 90° with respect to the emission axis of the signal source, one third photodiode receiver PD3 being placed at about 45° with respect to the emission axis of the signal source, one fourth photodiode receiver PD4 being placed at about 0° with respect to the emission axis of the signal source. Of course, more (or less) than 4 receivers may be used depending on the specific need and more than one receiver may also be placed at the same angular degree with respect to the emission axis 54 of the optic fiber. More specifically all the detectors 57 are arranged on a same plane, which in turn coincides with the plane at which the source 53 is arranged. This allows to realize a spatial diversity of detection, which, when present, cooperates with the multiple wavelength emission of optical radiation to further increase the quality of reading of the heartbeat and renders the sensor 100 more robust to external radiation influences. Each detector 57 is configured to receive the signal emitted by the signal source (and duly reflected, scattered or transmitted) radially along the normal section of the blood flow in the tube of the extracorporeal blood treatment apparatus. The new measurement system extends the architecture of the traditional design to collect light at different geometrical angles with respect to the emitter, allowing for discrimination between reflected, scattered and transmitted light. A loss in transmitted light due to an increase in scattering is not falsely detected as an increase in absorbance, if, at the same time, the scattered light is picked up by a different receiver. In order to achieve the above configuration, each detector 57 includes a respective optic fiber 59, one end being placed in correspondence of the segment 61, the other end being coupled to a receiver, in detail a photodiode receiver. In more detail, the end of the fiber optic 59 in correspondence of the segment 101 is fixed to the housing 51 and is placed at the counter-shaped portion and faces the segment 101 in a coupling condition of the housing with the segment 101. As mentioned, all channels for receiving the signals are placed radially along the normal section of the blood flow, except for the reflection channel (0°) which is slightly shifted along the flow direction to allow placement of the emission fiber 56. Both emitted and collected optical radiation is coupled to and from the segment 101 using e.g. plastic optics fiber (ESKA GH4001, Mitsubishi Rayon). Photodiode receivers 58 may have a specific fiber-coupling mechanics (e.g. IFD91, Industrial Fiber Optics, Tempe, USA) for light collection channels, corresponding to PD1-4 in FIG. 3.

The photodiode receivers 58 are housed on a printed circuit board 60a along with analog circuitry for transimpedance amplification 62; the circuitry for transimpedance amplification 62 includes a current-to-voltage converter (for example implemented using an operational amplifier). The circuitry 62 may be used to amplify the current output of the photodiode receivers 58. Current-to-voltage converters are used with photodiodes that have a current response that is more linear than the voltage response (it is common for the current response to have better than 1% linearity over a wide range of light input). The transimpedance amplifier presents a low impedance to the photodiode and isolates it from the output voltage of the operational amplifier. There are several different configurations of transimpedance amplifiers, the one factor they all have in common is the requirement to convert the low-level current of a sensor to a voltage. The printed circuit board 60a further includes low-pass filtering stage 63 and gain-stage amplification. The cutoff frequency of the lowpass filter 63 is set to e.g. 30 Hz. This helps to reduce unwanted noise that may affect the signal processing that is performed on the output signal 200R which is produced by the detector. Lowpass filter 63 may be further set at a lower frequency, e.g. at less than 10 Hz, particularly equal or less than 5 Hz or 4 Hz, to further limit the upper bandwidth of the output signal 200R. The gain is set to channel-specific values, based on preliminary testing and calibration. The analog signals are then converted into digital signals by a suitable converter 64. More in detail, the analog outputs are sampled at a rate of 100 Hz with 12-bit resolution using an NI USB-6008 DAQ card (National Instruments Italy Srl, Milano, Italy) and recorded by a custom LabView Virtual Instrument. The multi-LED emitter, the signal conditioning board and the DAQ card were assembled together on a 3D-printed housing and placed inside a grounded metallic box (see FIG. 3) for electromagnetic shielding, provided with openings for fiber optics 56, 59, data connection and power supply. In a particular embodiment, each of the detectors 57 is configured to receive an optical radiation at a predetermined wavelength or in a predetermined frequency window. More in detail, the first detector 57 (PD1) is configured to receive optical radiation at the first wavelength $\lambda_1$, or into a first frequency window comprising said first wavelength, the second detector 57 (PD2) is configured to receive optical radiation at the second wavelength $\lambda_2$, or into a second frequency window comprising said second wavelength, the third detector 57 (PD3) is configured to receive optical radiation at the third wavelength $\lambda_3$, or into a third frequency window comprising said third wavelength and the fourth detector 57 (PD4) is configured to receive optical radiation at the fourth wavelength $\lambda_4$, or into a fourth frequency window comprising said fourth wavelength. The several wavelengths of radiation above described may be used to detect flow variations through the more or less specific analysis of flow of hematocrit and osmolarity; since the effects of osmolarity may be detected and decoupled, also a better estimation of blood volume variation may be obtained. Using several channels for detecting the radiation at different wavelengths allows for determining and removing unwanted effects and still better allows to detect the heartbeat because the influence in the overall transmission of radiation is given by two different properties of the blood. It may result that variations at least of the amplitude of the received optical radiation in some channels could be more sensitive to specific parameters, while the behavior of other channels is more like a mix of properties (hematocrit and osmolarity). The digital signals are input to a controller 65 for being used in detecting the heartbeat and the heart rate through the tube segment 61 of the extracorporeal blood treatment apparatus, as apparent from the following detailed description.

Signal Processing and Method for Detecting Heartbeat

The Applicant has understood that a (e.g. optical signal) response signal measured from a (e.g. optical signal) detector in a procedure for heartbeat detection is affected at least by red cells concentration resulting from the pulses the heart provides. As well said red cell concentration is affected also by the pulses provided by the cyclic operation of the peristaltic pump. The Applicant has further discovered that the informative signal received by the detector(s) 57 is substantially not altered by, and/or is substantially not related to or is substantially not function of, size and/or geometry variations of at least a part of the segment 101 at which said information signal is received, said size and/or geometry variations being the results of said flow perturbation of the blood flowing in the segment 101. This means that even if the segment 101 may enlarge and/or be deformed as a result of the flow peaks induced by the heart or, most of all, by the operation of any of the pumps of the apparatus, the reliability and precision of detection of the proper heartbeat frequency is finally substantially not affected. In this sense it is remarked that detecting the heartbeat frequency in accordance to the present disclosure allows for lessening the requirements of the materials and/or design of the segment 101, which may be very hard or, on the contrary soft; in contrast, reading the heartbeat frequency through any measurement of the heartbeat through evaluation of the deformation of the segment 101 may require significant consideration of the materials and sizes used for dimensioning the segment 101.

Figure 4:
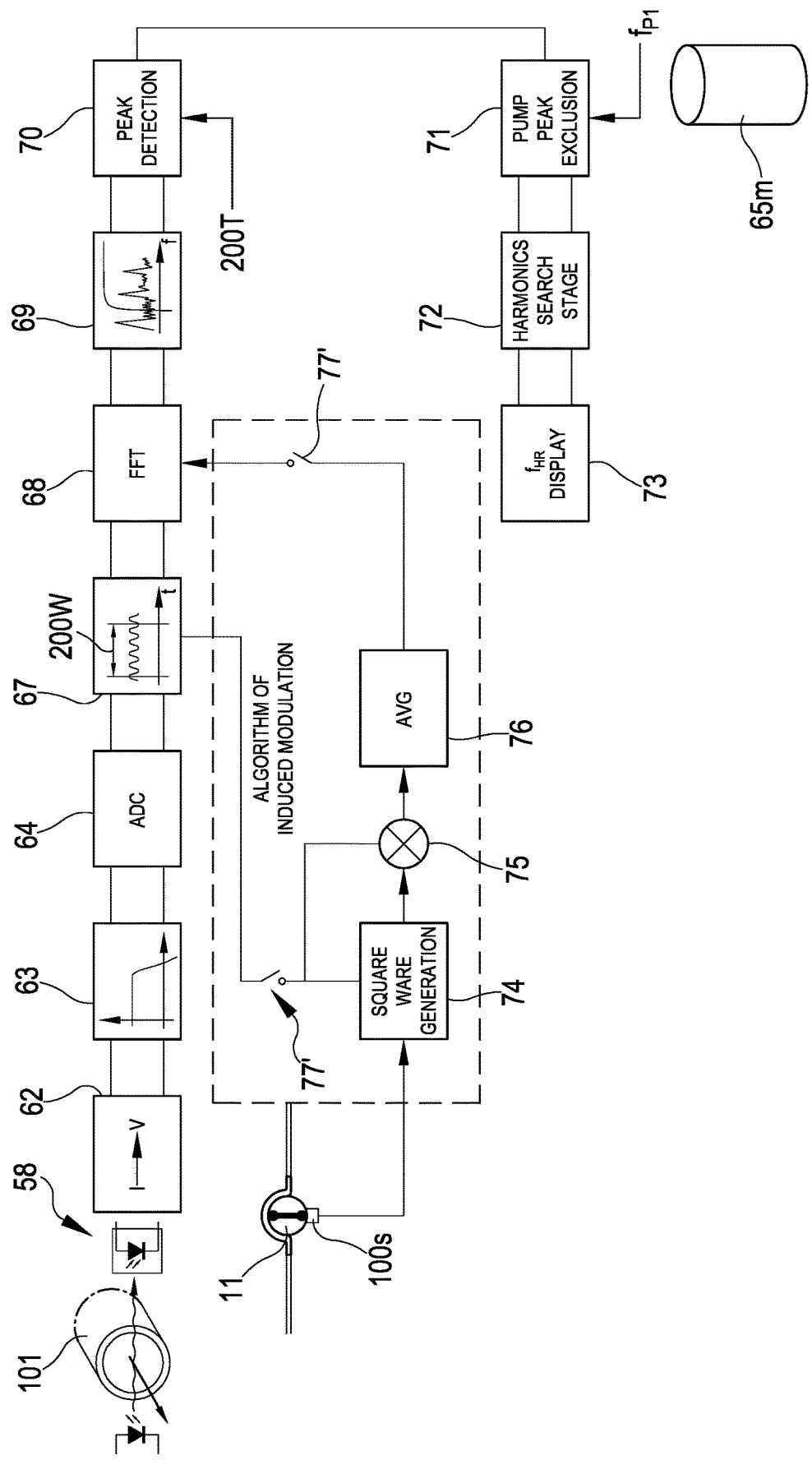
FIG. 4 shows a schematic block diagram of the signal processing operations performed through the sensor object of the present disclosure.

FIG. 4 shows a block scheme of the principal operations of signal processing performed through the sensor 100 according to the present disclosure; it may be noted that said processing is hereinafter described as being performed by the controller 65. This shall not be intended as limiting, since at least part or any part of the signal processing may be performed by a data processing unit which is different than the controller 65 and may be arranged outside the body of the sensor 100. It may be further noted that while today's technology allows for performing at least part of the signal processing herein described via software, e.g. via a software loaded on a memory electronically accessible by e.g. the controller 65 also this aspect shall not be considered as limiting, since at least part of the processes and steps of the subsequent following description may be made or carried out by physical, i.e. hardware, stages, which are depicted in FIG. 4. As depicted in FIG. 4, after the photodiode receiver 58, a transimpedence amplifier 62 is arranged to transform the current driven signal generated by said detector 57 to a voltage driven output signal. The output of the transimpedence amplifier 62 feeds the input of the low-pass filter 63 whose output in turn feed the inputs of the analog-to-digital converter 64, which performs a sampling of the signal, transforming it so that the output signal to be further electronically process is in the numeric domain.

Figure 5:
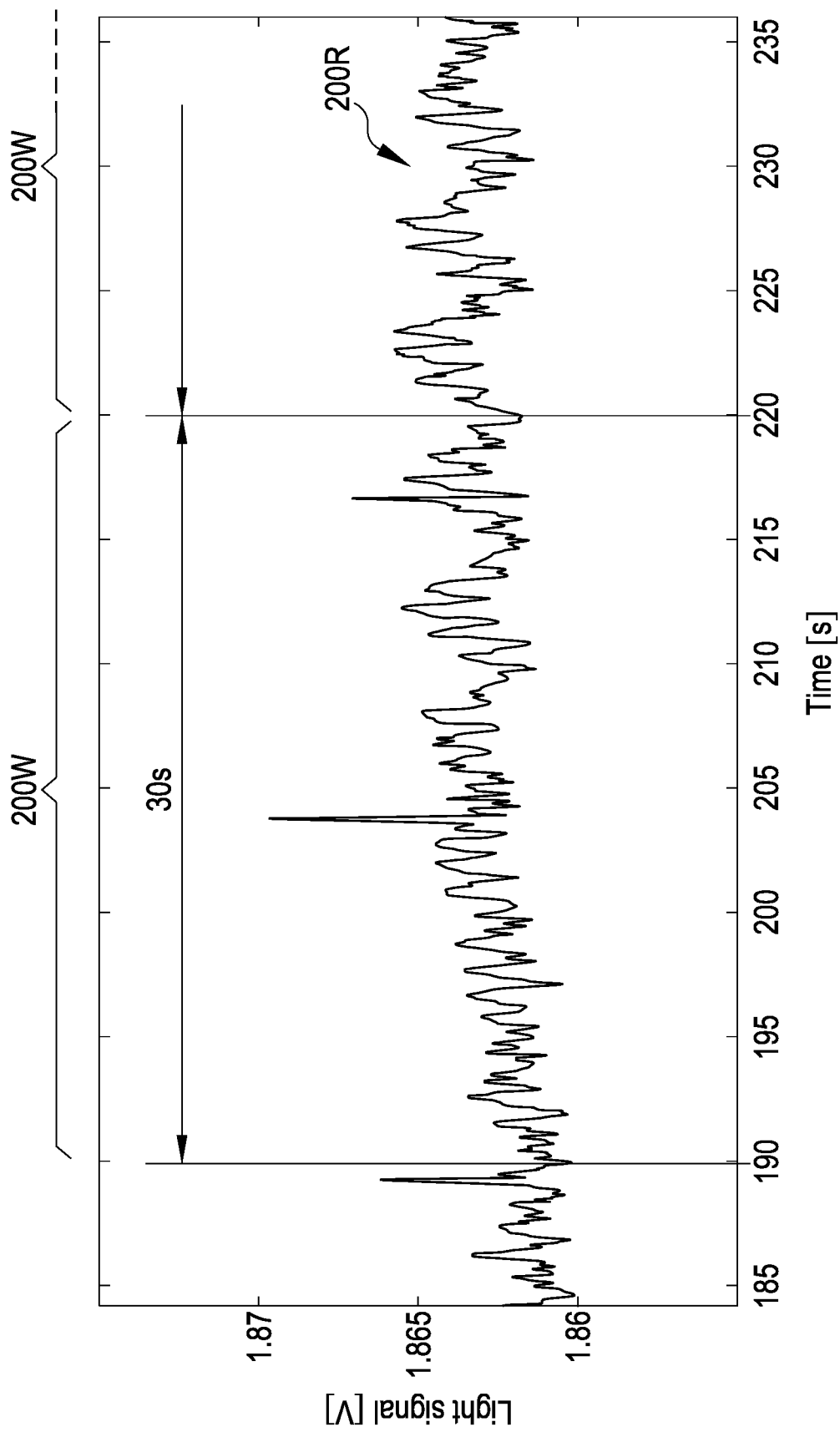
FIG. 5 shows an exemplificative diagram of an output electric signal provided by a detector part of the sensor according to the present disclosure.
Figure 7:
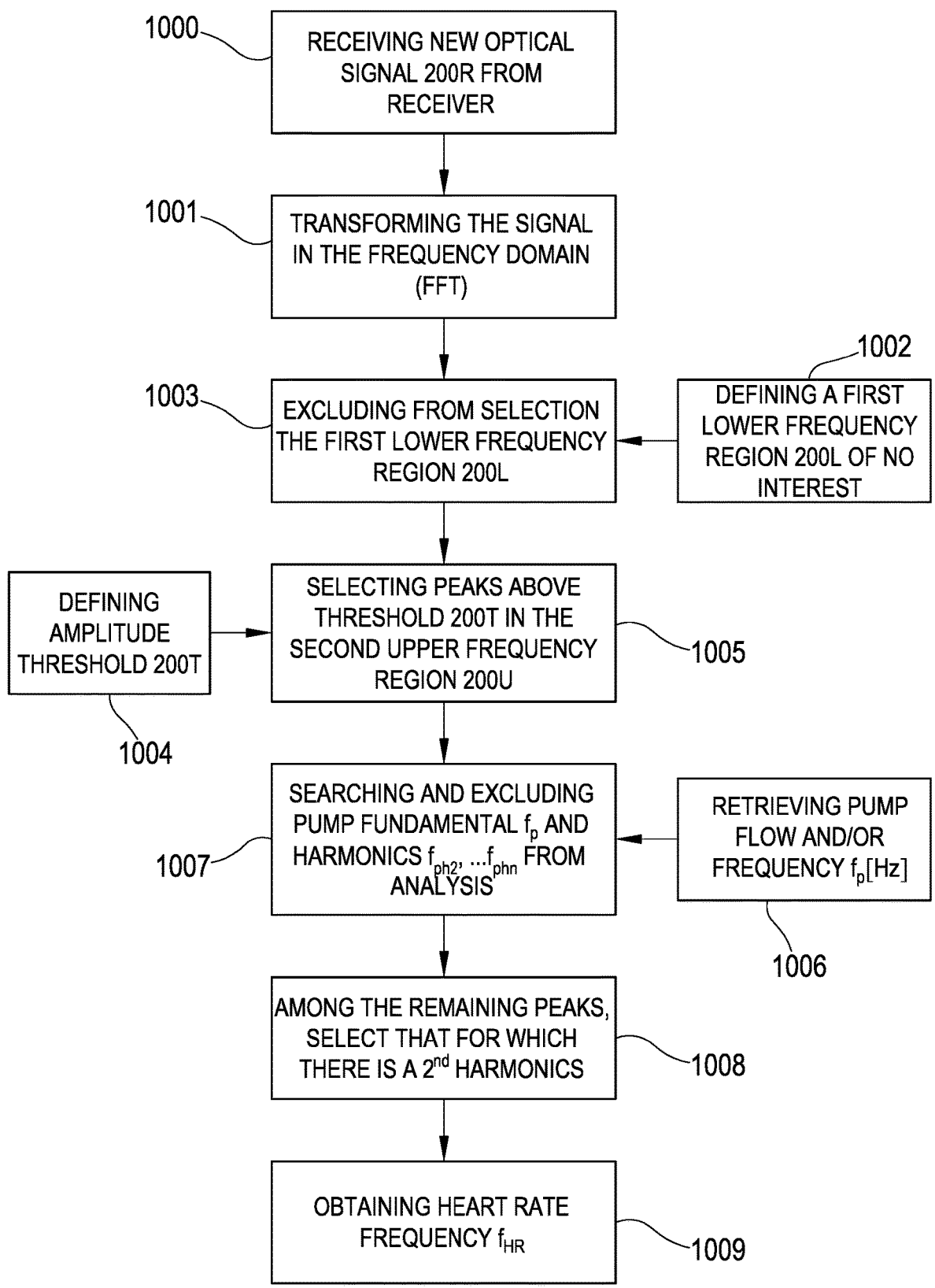
FIG. 7 shows a flow chart showing steps of a method for detecting heartbeat and/or heart rate through the non-invasive sensor of the present disclosure.

As schematically shown in FIG. 5, and as reported in the brief flow-chart of FIG. 7, a output signal 200R, produced as an output after the receipt of the optical signal passed through the blood and the segment 101 (this steps corresponding to block 1000 of FIG. 5), is first of all sampled into a reference window of sampling 200W of a predetermined length. FIG. 5 shows an example wherein said window is 30 s long, but this example shall not be intended as limiting since the reference window of sampling 200W may have for instance a length equal or less than 1 minute long, or equal or less than 45 s long, or equal or less than 30 s long, or equal or less than 20 s long, or equal or less than 15 seconds long or equal or less than 10 s long. The portion of the output signal 200R contained within said window will be hereinafter referred as the reference part of the output signal 200R. It shall be noted that the more the window is long, the higher the results of the processing are averaged. Albeit lengthening the window may have positive effect in averaging occasional spikes of noise in the output signal 200R, excessive window length should be discouraged in order to reduce the risk of significant variation of the frequency of heartbeat therein, which could compromise the quality of reading of the heart frequency and of the subsequent processing to which the signal is subject.

Should the controller 65 be made through hardware processing stages, the windowing of the output signal 200R into a reference window of sampling 200W of a predetermined length may be performed by a time-domain windowing stage 67, operating on numeric signals, whose input is fed, in particular directly fed, by the output of the analog-to-digital converter 64.

The output signal 200R of FIG. 5 is not only containing the information of the heartbeat carried out by the flow pulses induced by the heart of the patient, but also an unwanted noise, including undesired noise that is produced by the peristaltic blood pump 11 operating for forcing the flow of the liquid into the blood circuit, in particular into the segment 101. More in detail, FIG. 5 is the result of a raw (non-filtered) signal in output of the detector with the following test conditions:

fluid flow in the segment 101 with the peristaltic blood pump 11 set at 200 ml/min, that for the reference apparatus 1 used for the test results in an unwanted pump noise whose frequency is around 1.0 Hz;

fluid flow in the segment 101 with a cardiac simulator set at 70 bpm, whose nominal frequency substantially corresponds to 1.16 Hz.

Subsequently, through the controller 65, a further electronic processing of the signal is performed. In particular, the output signal 200R, and in particular its relevant portion into the aforementioned window, is subjected to a transformation in the frequency domain, for instance through the application of a Fourier transform, in particular a fast Fourier transform (this step corresponds to block 1001 in FIG. 7). It shall be noted that the fast Fourier transform may not be the only way to calculate the transformation in the frequency domain, but it is that selected by the Applicant since one the exemplary embodiments herein disclosed works on an output signal in the numeric domain, since being converted thereto through the analog-to-digital converters previously disclosed.

Figure 6:
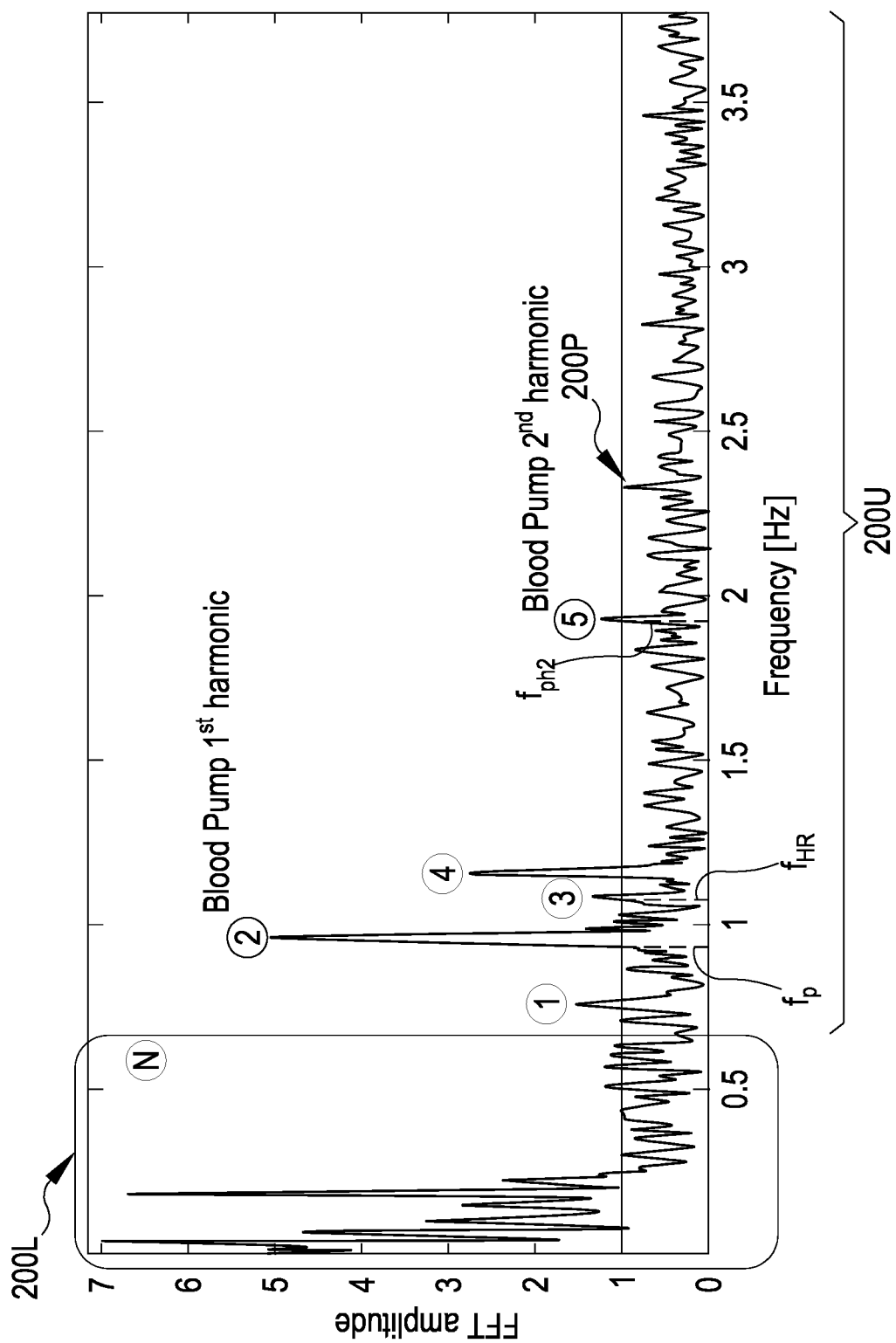
FIG. 6 shows a frequency-domain diagram showing the combined spectrum peaks of background noise, noise induced by the operation of at least one pump of the apparatus, and peaks relating to the actual blood pulses provided by the heart, as detected through the sensor of the present disclosure.

FIG. 6 shows an exemplary diagram of the spectrum of the signal of FIG. 5 once converted from the time domain to the frequency domain. Should the controller 65 be made by hardware signal processor stages, the step of transformation of the windowed reference part of the output signal 200R from the time domain into the frequency domain is made through a Fourier transform stage 68, particularly a stage performing a processing according to the FFT algorithms, whose inputs are directly fed by the output of the time-domain windowing stage 67. The upmost frequency of the spectrum under exam is set to 4 Hz; this is done e.g. through the low-pass filter stage 63 in the time domain, or may be otherwise made by a hard-cutting of the Fourier transform at the aforementioned frequency; choice of a low upmost frequency for the electronic processing of the spectrum is done since the search for the heartbeat is performed considering the fundamental and the 2nd harmonics thereof, which physiologically and/or typically in the normal resting condition at which the patient is during the treatment, do not exceed 4 Hz. Anyway, as a precautionary measure, upper frequencies may be chosen, e.g. as up to 30 Hz as previously disclosed when discussing the operation of the lowpass filter 63. It is noted that below 0.3 Hz, the amplitude of the spectrum rapidly increases. Once more, Applicant has considered that the fundamental frequency of a physiologically beating heart, at least in the resting conditions at which the patient stays during the treatment, are not below 0.6 Hz, or 0.5 Hz, or 0.4 Hz or even 0.3 Hz. The Applicant has chosen therefore to select electronically a first lower frequency window 200L which contains portions of spectrum not of relevance for the present detection, and an upper frequency window 200U which starts with a lower frequency just above the highest frequency of the lower frequency window 200L. This latter, in the diagram of FIG. 6 is 0.6 Hz. The lower frequency window 200L is cut out from further signal processing; this helps in analysing a portion of spectrum free from highly relevant unwanted noises, which has been proved to be in the bottom, lowest part of the spectrum and may be for instance due to the flow of the blood within the segment 101, to breathing and/or other physiological or external 'disturbances'. Any relevant data concerning the lower frequency window 200L limits, e.g. the upper frequency of the lower frequency window 200L, and/or any relevant data concerning the upper frequency window 200U, e.g. the lowest and the upmost frequencies thereof, may be conveniently stored in a memory 65m, arranged within the body of the sensor 100 or otherwise operatively accessible at least by the Fourier transform stage 68. The window of interest is then the upper frequency window 200U, which in the exemplary diagram of FIG. 6 starts at a lowest frequency of 0.6 Hz and ends with an upper frequency of 4 Hz. In those regions substantially lies any physiological cardiac fundamental frequency, its 2nd harmonic, and—the case may be, as depicted—the fundamental and at least the 2nd harmonics of the peristaltic pump 11. Actually, the diagram of FIG. 6 shows relevant peaks which are marked with circled reference numbers "1", "2", "3", "4" and "5". Among them, the fundamental frequency of the pump 11 is marked with the reference frequency "$f_p$", and its 2nd harmonics is marked with the reference frequency "$f_{ph2}$"; as it may be seen the fast Fourier transform of FIG. 6 shows the fundamental frequency $f_p$ of the pump 11 just below 1 Hz and its 2nd harmonics just below 2 Hz. The selection of the upper frequency window 200U, or otherwise filtering out the lower frequency window 200L may be performed by an upper frequency window selection stage 69, in case the controller 65 comprises hardware signal processing stages. It may be noted that the upper frequency window selection stage 69 actually behaves as a high pass filter, or a band-pass filter whose lowest frequency substantially coincides with the upmost frequency of the lower frequency window 200L. The inputs of the upper frequency window selection stage 69 are fed by the output of the Fourier transform stage 68; the outputs of the upper frequency window selection stage 69 feed a peak detection stage 70 whose operation will be clarified in the following part of the description.

The heart beat fundamental frequency, as it will be clearer through reading the subsequent part of the description corresponds to peak "3" in the spectrum, and the frequency is marked with the reference name "$f_{HR}$". It is herewith noted that the diagram also shows a 2nd harmonics of this heartbeat frequency, whose peak is designated by the reference number 200P. It is noted that up to this step, the frequency of the heartbeat is still not known, and is retrieved after some other processing steps are performed. Actually the pump 11 fundamental frequency—and thus its 2nd harmonics which as any 2nd harmonics nominally lies at the double of the fundamental—is known, to the controller 65. In fact, any apparatus 1 is provided with a specific pump 11, in particular a specific set of pumps in case many of them are present, which for any presettable flow rate [l/min] turn at a predetermined angular speed, i.e. their rollers cyclically compress and let expand a portion of tube at a predetermined frequency. Thus, it may be one of the following case:

in case a finite preset table of flow rates may be set for the operation of the pump 11, the bi-univocal relation flow rate/frequency is tabled in a table stored in advance in a memory operatively accessible to the controller 65;

in case a non-definite flow rate may be set by the user according to his wish, a sensor, e.g. a Hall sensor, may be arranged on the apparatus, in particular in substantial correspondence of the pump, in order to directly detect the operative frequency of the pump itself. Resuming, this part of the signal processing, as schematically marked in block 1006 of the flow-chart of FIG. 7, comprises in general retrieving the operation frequency of the pump 11 which forces the fluid flow into the relevant segment 101 at which the sensor 100 is coupled, and this retrieving may be electronically performed through a direct sensing or a loading of a value from a table. It is thus apparent the peaks referred to in FIG. 6 with references "2" and "5" may be clearly identified and then discarded by further electronic processing. In other words, the electronic processing performed by the controller 65 comprises (block 1007 in the flow chart of FIG. 7) a search and exclusion of the pump 11 fundamental frequency $f_p$ and any of its harmonics $f_{ph2}, f_{ph3}, \ldots f_{phn}$. Should the controller 65 be made using hardware processing stages, this latter operation may be made by a pump peak exclusion stage 71, whose inputs are fed by the output of the peak detection stage 70.

A particular embodiment of the processing therein disclosed involves setting a threshold 200T of spectrum amplitude before searching any peaks of amplitude. Said threshold value 200T may be fixed in time, or otherwise adaptive. In FIG. 4 this operation is schematically represented by the input 200T of the peak detection stage 70 which is fed by the output of the upper frequency window selection stage 69. Albeit a careful selection of appropriate values of threshold may be performed, Applicant shows that the application of a threshold allows for reducing the computation burden of the controller 65 and reduces the risks of false readings, provided that only peaks whose amplitude rests beyond the threshold 200T are considered as potential useful signal frequencies; this helps to reduce the risk of reading a peak of noise as an actual heartbeat.

According to the application of the threshold, which according to FIG. 5 is set at a reference value 1 in the spectrum, only peaks identified by markings "1", "3", "4" could be of a potential interest.

Then the controller 65 performs a further electronic processing in the spectrum taking into consideration any peak beyond (i.e. above) the threshold 200T (we hereby call it peak under test) and considering the presence of another peak at exactly the double of the frequency at which the peak under test lies. Then for every peak under test, whose amplitude is beyond the threshold 200T (particularly moving from lower to upper frequencies):

if a peak 200P is found at a frequency corresponding exactly to the double of the frequency of the peak under test, this means that the peak under test corresponds to the sought heartbeat signal, and thus to the frequency of said peak is assigned the reference $f_{HR}$;

if no peak is found at a frequency corresponding exactly to the double of the frequency of the peak under test, this means that said peak under tests does not correspond to the sought heartbeat signal and thus does not correspond to the heartbeat; in this case, the algorithm proceeds in taking into account another peak whose amplitude is beyond the threshold 200T (if present).

Those operations are carried out by the harmonics search stage 72, in case the controller 65 is designed to perform such operations with a hardware processor; as depicted in FIG. 4, the harmonics search stage 72 is fed in input by the output of the pump peak exclusion stage 71. The harmonics search stage 72 is provided with an output that is configured to produce a signal representing the value of the reference frequency $f_{HR}$ of the heartbeat. This reference frequency may be provided on a screen which is schematically represented by the $f_{HR}$ displaying stage 73 in FIG. 4.

In a particular albeit non-limiting embodiment, the electronic search of the peaks in the spectrum of the signal at the double of the frequency at which the peak under test lies is may be performed also keeping into consideration the peaks that lie below the threshold 200T level. This helps in reducing the risk of discarding an actual peak corresponding to the 2nd harmonics of the heartbeat. This step corresponds to the block 1008 of the flow-chart of FIG. 7. The heartbeat frequency $f_{HR}$ so obtained is then stored at least temporarily in a memory electronically accessible to controller 65, and particularly is provided as, or into, an electronic signal to be transmitted to a monitor or display of the apparatus 1, in order to let the user know the heart rate (block 1009, flow-chart of FIG. 7). The heart rate frequency may be transmitted by the controller 65 or by any other electronic device operatively connected thereto to a remote device, e.g. a smartphone or a laptop computer, particularly using a wireless channel whose electromagnetic behaviour is compatible (and does not interfere) with the medical applications.

In the case of FIG. 6 only the peak with the reference "3" is the peak to which actually corresponds a further peak at exactly the double of its frequency. Peaks "1" and "4" are peaks due to noise captured by the detector 57, and do not actually correspond to a heartbeat. Through the algorithm carried out by the controller 65, the system is capable of discriminating very well between noises and real heartbeat frequencies even if they fall very close one another and even if the noise peaks exceed the magnitude of the peak which actually corresponds to the heart rate. In the case of FIG. 6, in fact, peak "4" is less than 0.1 Hz far from the actual heartbeat frequency, and even if its amplitude is almost two times higher than the amplitude of the peak corresponding to the actual heartbeat, this latter may be actually detected and peak "4" is actually discarded.

Detection of the peaks in the spectrum of the pump is performed by a step of processing the output spectrum with an algorithm of peak detection; in a non-limiting, embodiment, the peak detection comprises, moving from lower frequencies to upper frequencies, calculating the derivative of the spectrum signal for detecting and at least temporarily storing the frequencies at which the derivative change sign from positive to negative (this being indicia of the peak); Said temporary storing, which is performed in a memory electronically accessible by the controller 65, e.g. an internal memory, is performed by virtue of an electronic table for which a first column represents the values of the peak frequencies sought through the peak detection algorithm and for which the second column represents the corresponding amplitude values. Thus a table similar to the exemplary one that follows may be stored in said memory.

| Frequency [Hz] | Amplitude |
|---|---|
| $f_{1p}$ | $A_{1p}$ |
| $f_{2p}$ | $A_{2p}$ |
| ... | ... |
| $f_{np}$ | $A_{np}$ |

In another solution, seeking the peaks in the output spectrum may be performed through a moving-windows algorithm. In the moving window algorithm, a predefined width frequency window of exam is considered and is made moving e.g. from the lower to the upper frequencies of the reference spectrum, e.g. from the lower to the upper frequencies of the upper frequency window 200U. It may be noted that the controller 65 may be configured to make electronically the window move in a stepped way. For each step of motion of the window, the local maximal amplitude of the spectrum is considered, and its corresponding frequency is tabled in a way similar to that before. It may be noted that is convenient that in every step the frequencies of the moving window do not superimpose with frequencies of the moving window at the step before. When the controller 65 is made through hardware processing stages, those operations are conveniently made by the peak detection stage 70 and/or by the harmonics search stage 72. It is noteworthy that the algorithm herein disclosed, even with a low-computation power processing unit, allows to substantially obtain the heart rate in real time and in a substantially reliable way, without any relevant delay especially if after a set-up period e.g. for obtaining the first window of signal in the time domain.

Induced Modulation Algorithm

Figure 8:
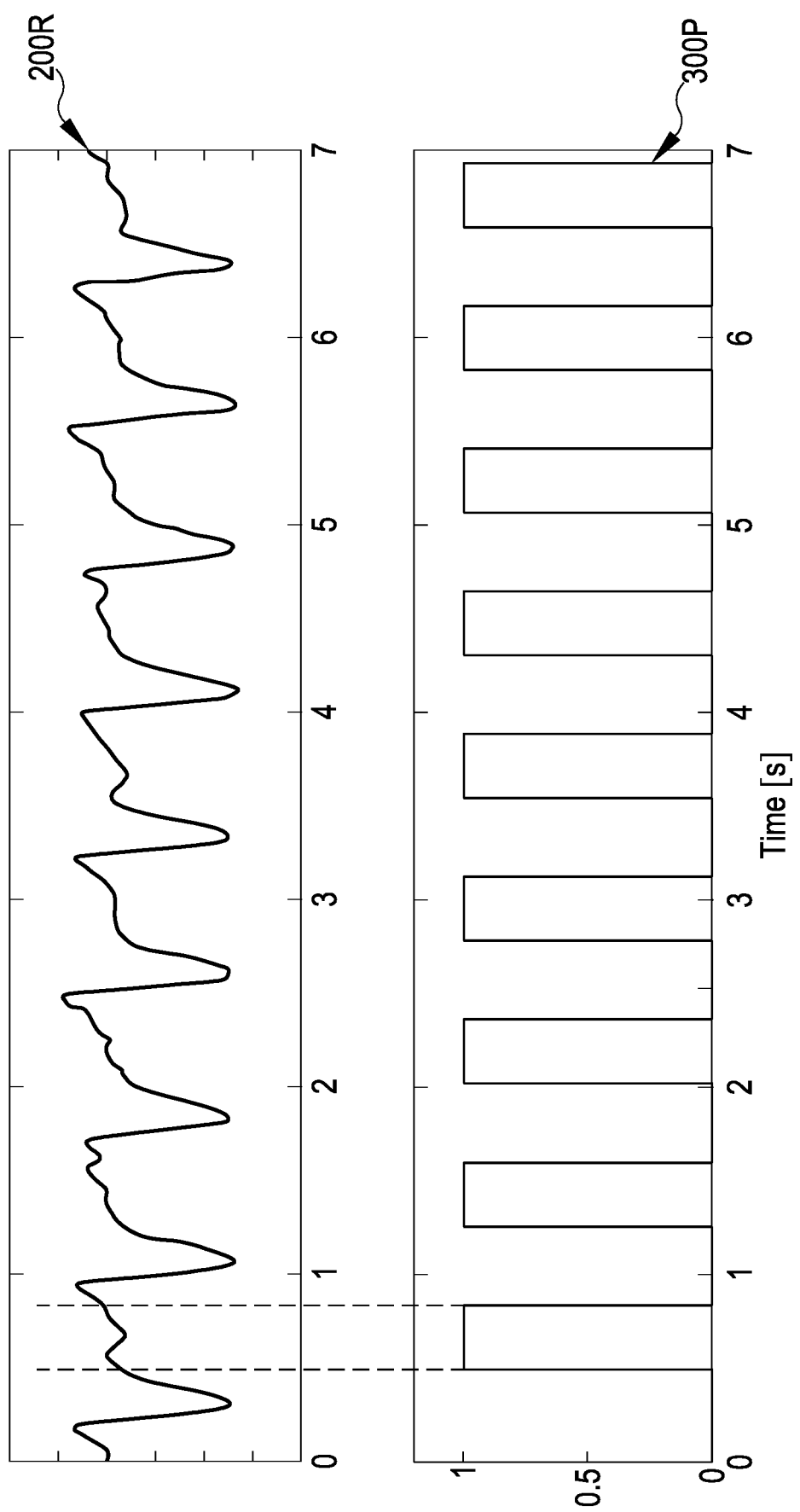
FIG. 8 shows a combined diagram of a raw signal corresponding to the output signal of a detector of the sensor according to the present disclosure, and a pump-associated square-wave signal used to process the output signal.
Figure 9:
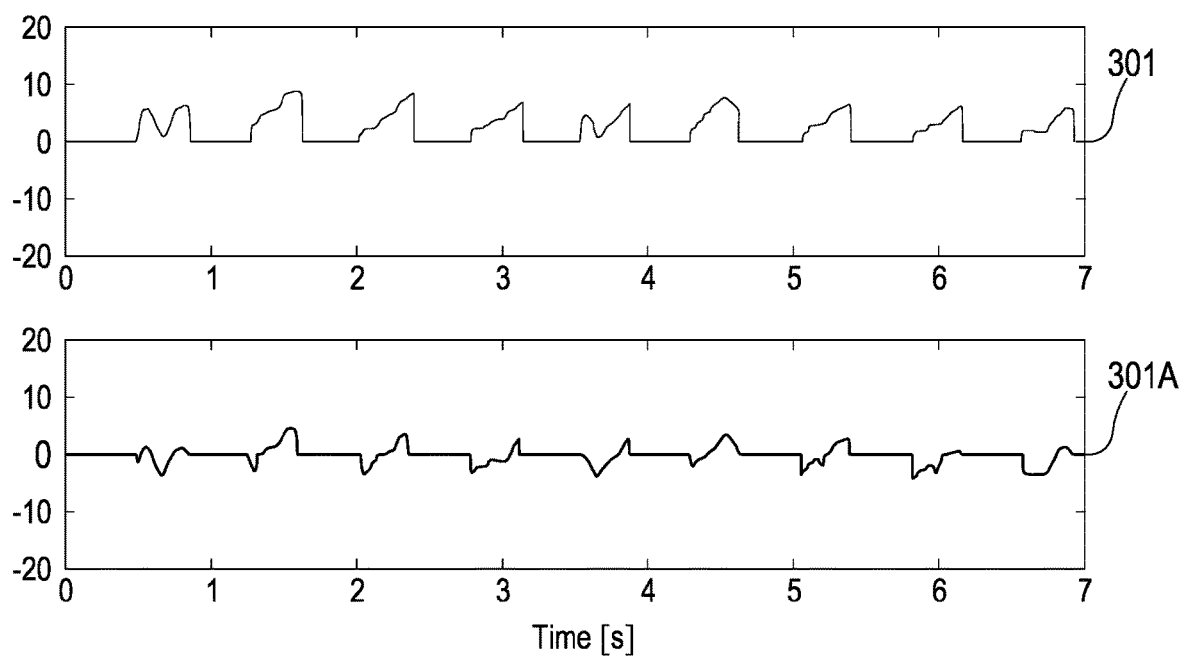
FIG. 9 shows a combined diagram wherein the upper part represents a resulting signal product of the multiplication between the output signal and the pump-associated square-wave signal, and wherein the lower part represents a further signal corresponding to the above signal after the average value of the non-zeroed parts has been removed.
Figure 11:
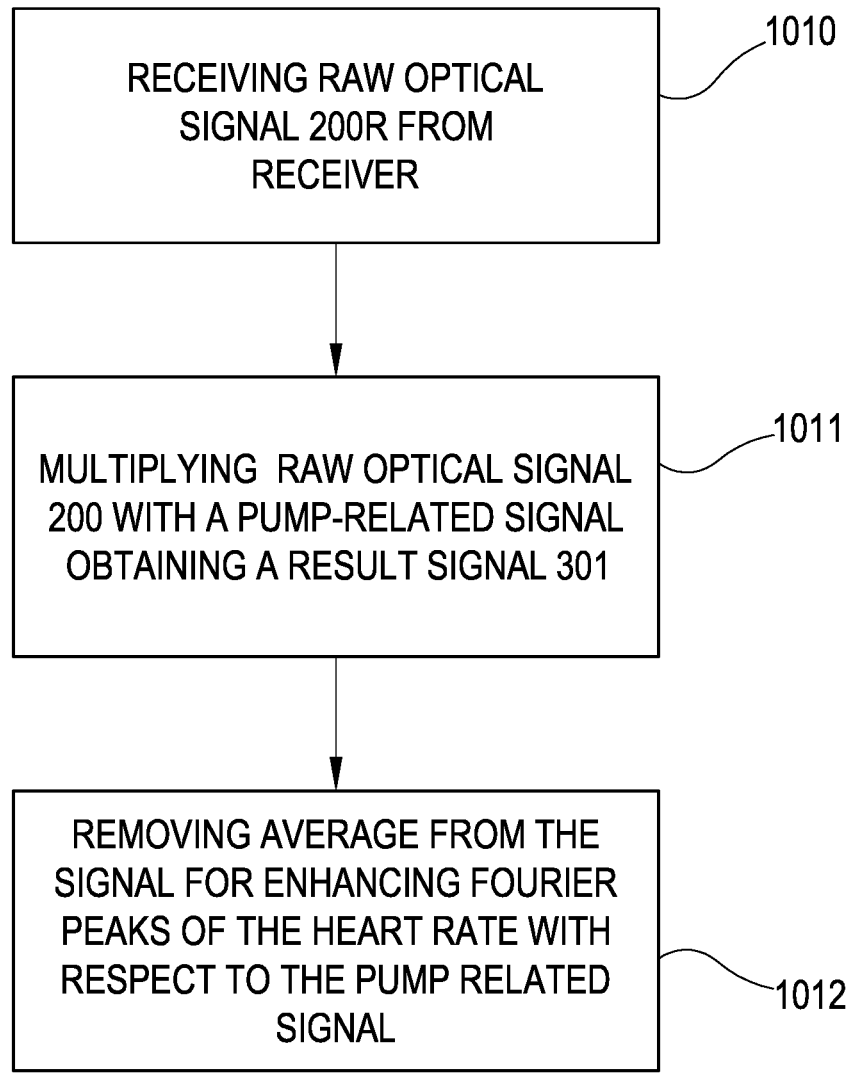
FIG. 11 shows a schematic flow chart of the method disclosed in FIGS. 8, 9 and 10.

Applicant has further considered that reliability of reading of the correct heartbeat frequency $f_{HR}$ could be performed by applying the following electronic signal processing to the signal in output of the detector 57. The following steps of signal processing, which conveniently may be carried out by the controller 65, are to be performed before the step of transformation of the output signal of said reference window of sampling 200W into the frequency domain. This means, that considering the flow-chart diagram of FIG. 7, the steps that will be hereinafter described will lie between block 1000 and block 1001. The Applicant has discovered that reliability of reading of the correct heartbeat frequency $f_{HR}$ even in presence of strong noise signals e.g. induced by the pump 11 operation, may be further increased by processing the output signal 200R so that when the spectrum analysis is performed, the peaks in frequency corresponding to the heartbeat are provided with an amplitude which is amplified with respect to the amplitude of the peaks of the noise (these latter resting unaltered) or, correspondingly, so that when the spectrum analysis is performed, the peaks in frequency corresponding to noise see an amplitude which is attenuated with respect to the amplitude of the peaks in frequency corresponding to the heartbeat. At first, this algorithm involves electronically multiplying, in the time domain, the output signal 200R produced in output by the detector 57 (block 1010, FIG. 11) with a pump-associated signal 300P whose shape is cyclic and/or repeated in time, and is correlated to the pump cycle point; FIG. 8 shows an example of a couple of diagrams wherein the output signal 200R (upper diagram) is multiplied by said pump-associated signal 300P (lower diagram). The step of multiplication corresponds to block 1011 of FIG. 11. In general terms, the pump-associated signal 300P is periodically zeroed in correspondence to portions of time wherein the pump provides pulses of flow at least in the segment 101 at which the sensor 100 is arranged. Conveniently, in an embodiment which is depicted in the lower diagram of FIG. 8, the pump-associated signal 300P is a square wave, with a predetermined duty cycle, which for every cycle is provided with a first portion of unitary amplitude and with a second portion which is zeroed. The first portion clearly corresponds to the portions of time wherein the pump does not provide pulses of flow. Multiplication of the output signal 200R by the pump-associated signal 300P results in a production of a result signal 301 whose shape is represented in the upper diagram of FIG. 9. Clearly also the result signal 301 is characterized by portions which are zeroed in correspondence to the same portions of time wherein the pump-associated signal 300P is zero. It is noted that using a square wave allows for not altering the shape of the output signal 200R in the non-zeroed portion, and this contributes to keep unaltered the spectrum thereof. Subsequently, as schematically represented by block 1012 of the flow-chart of FIG. 11, an electronic calculation of the average magnitude $V_m$ of the result signal 301 is calculated for the non-zeroed portions, or more in general across a window of a predetermined time length. The average magnitude $V_m$ value is then subtracted to the result signal 301, in particular only in correspondence of the portions which are non-zeroed, so that to produce an averaged signal 301A whose shape is reported in the lower diagram of FIG. 9.

Figure 10:
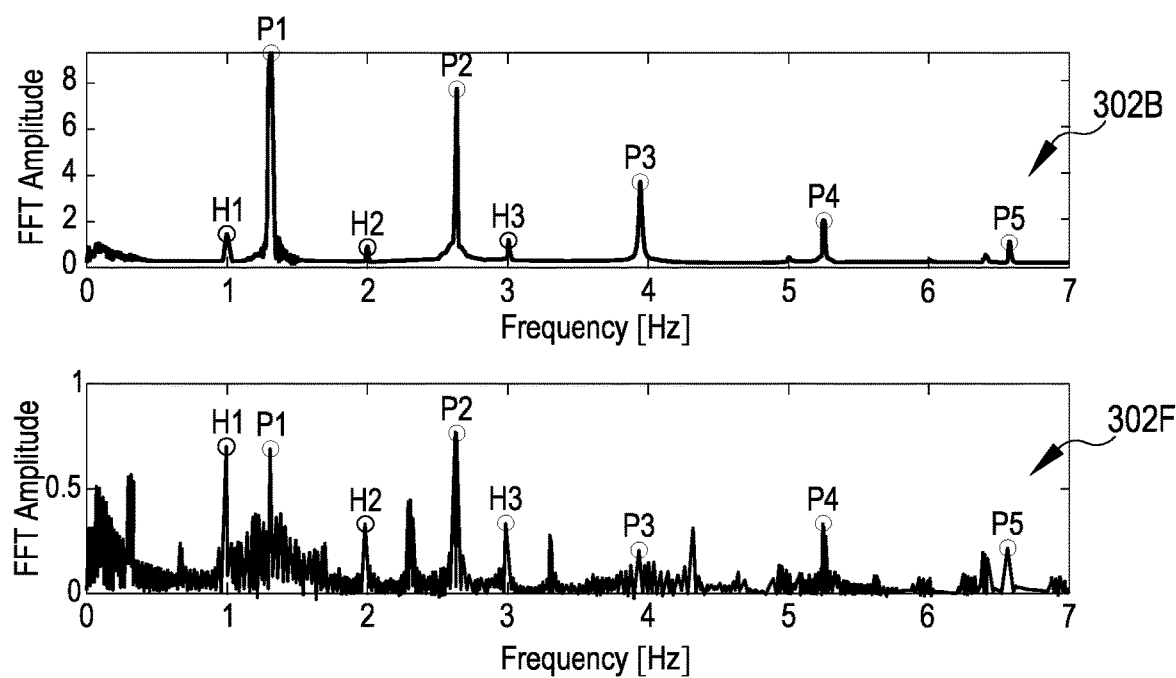
FIG. 10 shows a combined diagram wherein the upper part represents a frequency-domain spectrum of pulses induced by the pump and by the heart, as read by the sensor according to the present disclosure, without the processing of the raw output signal as schematically shown in FIG. 8 and in FIG. 9, and wherein the lower part represents the result of the processing of the output signal of the detector following the procedure of FIG. 8 and of FIG. 9, wherein it is possible to see how the peak pulses relating to the blood pulses induced by the heart have then a magnitude significantly higher than before, now being comparable in amplitude to that of the pump.

Hence a transformation in the frequency domain is performed on the averaged signal 301A, e.g. as previously disclosed. Further processing performed on the spectrum of the output signal is eventually performed on the average signal 301A spectrum. FIG. 10 clearly shows the effect of the induced modulation in terms of spectrum in frequency. While before the induced modulation the amplitude peaks of the noise induced by the pump 11 action (peaks P1, P2, P3, P4, P5, respectively corresponding to the fundamental, 2nd, 3rd, 4th, and 5th harmonics) are far higher than the peaks of the heartbeat (peaks H1, H2, H3, respectively corresponding to the fundamental, 2nd, 3rd harmonics) as up to 4 times higher, after the aforementioned processing of induced modulation is applied the peaks of amplitude of the heartbeat in the corresponding averaged signal 301A are enhanced. Thus, this lessens the requirements of proper threshold settings, and/or allows for a clearer identification of the correct heartbeat and allows for a more precise and reliable reading. It shall be noted that also the carrying out of the induced modulation algorithm above describe still allows to produce the indication of the heartbeat frequency $f_{HR}$ in a substantial real time.

It is herewith noted that the windowing process through the application of the predetermined length reference window 200W in the time domain is repeated cyclically moving the window for a predetermined amount of time or providing for buffering a new sample of reference portion output signal 200R to process as above described. Should the buffering stage so allow, the difference in time between two consecutive reference windows could be reduced at will, up to one single sample of delay. FIG. 4 depicts also this solution of induced modulation within the dashed box. Since the induced modulation is not compulsorily part of the disclosed algorithm of signal processing, two fictive switches 77' are depicted between the time-domain windowing stage 67 and the Fourier transform stage 68 to identify the optionality. In an embodiment, the controller 65 may comprise a square wave generator stage 74 which receives a first input from a pump cycle sensor 100s, in particular the Hall sensor coupled to the blood pump 11 and produces in output the aforementioned pump-associated signal 300P. Then, a hardware multiplier 75 arranged downstream the squared wave generation stage 74 multiplies the windowed reference part of the output signal 200R by the aforementioned pump-associated signal 300P, to obtain in output the aforementioned result signal 301 whose shape is represented in the upper diagram of FIG. 8. The aforementioned averaging operations may be performed by virtue of an averaging stage 76 of the controller 65, which is arranged downstream the multiplier 75 so that its output feeds directly the input of the averaging stage 76; the output of the averaging stage then feeds the input of the Fourier transforming stage 68. Applicant has finally provided for conceiving a subroutine of validation and enforcement of heartbeat reading, which comprises repeating at least part of the previous steps for a predetermined amount of times, e.g. three times. With a sufficiently short reference windowing, and thanks to the real time processing allowed by the algorithm herein disclosed, substantially we are in the conditions where the following hypotheses are made: 1) the flow rate of the pump 11 does not change throughout the above repetition, 2) the cardiac pulse rate rests substantially stable. Through the aforementioned repetition a series of n heartbeat frequency values $f_{HRn}$ is electronically calculated: $f_{HR1}$, $f_{HR2}$, $f_{HR3}$, in case of three repetitions. Those n (e.g. 3) values may be averaged together; the controller 65 could be configured to perform a discarding of at least one of the n frequency values, this one coinciding e.g. to that which more is distanced from the average values of the resting ones. Other statistic processing could be performed to the set of n heartbeat frequency values $f_{HRn}$.

Applicant has further noticed that during the blood treatment, which in normally quite long, the heartbeat frequency of the patient under treatment, even if in resting conditions, tends to have a (positive or negative) drift, due at least partially to the continuous change in its dynamic fluid conditions. This drift may result in a superimposition of the heartbeat frequency with the fundamental frequency of the pump. The controller 65 may be further configured to allow activation of a warning signal if the heartbeat frequency $f_{HR}$ is too close to the frequency $f_{P1}$ of operation of the pump 11. If during the blood treatment it is observed that, during the time, the heartbeat frequency $f_{HR}$ gets progressively too much close to the frequency $f_{P1}$ of operation of the pump 11, it activates a warning user signal (e.g. a visible and/or auditive alarm) for the user and optionally starts to record in a dedicated buffer all the recent amplitudes of the peak of the pump 11. This is warning condition, because if the cardiac frequency $f_{HR}$ gets substantially superimposed to the frequency $f_{P1}$ of operation of the pump 11, the present algorithm is no longer capable of distinguishing it. Applicant has further considered also this event, and provided for conceiving and configuring the controller 65 so that in this case, in addition to the activation of the alarm signal, the controller 65 sends an appropriate signal to the electric actuator of the pump 11 so that its speed (thus, flow rate, and frequency of operation) is changed, so that the resulting new frequency of operation results more distanced from the heartbeat frequency. In an embodiment, changing the speed and thus the flow rate and the frequency of rotation of the pump 11 is performed automatically in an iterative cycle of control performed by the controller 65; in order not to vary the total volume of blood which is treated during the whole session, the control unit may provide alternate changes of the pump blood flow rate (e.g., +/−30 ml/min) during the treatment session. Otherwise, the controller 65 may be configured to provide through the monitor of the apparatus 1 an indication to the operator for setting a new pump 11 speed, so that the change takes place manually.

Operatively a difference (or the absolute value thereof) is electronically calculated between the frequency $f_{P1}$ of operation of the pump 11 and the heartbeat frequency $f_{HR}$; the result of the difference is then compared to a reference value, and the control of the pump 11 is performed so that the resulting new frequency of operation of the pump 11 results more distanced from the heartbeat frequency. Another relevant advantage of the detection provided through the application of the algorithm for heartbeat detection herewith disclosed is that any sudden disappearance of the heartbeat may be easily detected. Applicant notices that disappearance of the heartbeat, i.e. a sudden condition wherein the sensor 100 no more detects any heartbeat frequency $f_{HR}$ may be the result of an unwanted disconnection of the venous port from the blood circuit 6,7, which may result in a gross leakage of blood that could result in an hypovolemic condition which may even affect life of a patient. For this purpose, an alarm signal may be produced in case a sudden lack of any heartbeat frequency is detected by the sensor 100, i.e. in case the sensor loses and/or is not able to detect any heartbeat frequency in accordance to the aforementioned disclosed process, in particular while in presence of the informative signal, i.e. while actually the optical source 53 is operative and/or while the detector 57 actually receives the informative signal with the pump signal but without any other useful signal with a 2nd harmonics within the conditions disclosed in the previous part of the description. Such alarm signal may be an electric signal transmitted to a user interface (e.g. monitor and/or loudspeaker) of the apparatus 1 for blood treatment or may directly be an acoustic or visible signal directly produced by the sensor 100 itself. Any part of the controller 65 may be made through a hardware data processing unit, in case comprising an arithmetic logic unit, suitable to perform at least part of the steps of the algorithms of signal processing herein described. In particular the controller may run an appropriate program, comprising software code portions which when executed by the controller 65 cause the execution of one or more of the steps disclosed in the present disclosure. The program may be referred as a software or firmware, and may be stored in a memory, in particular a non-transitory memory operatively, in particular electrically, accessible by the controller 65; said memory may be physically arranged within or outside the body of the sensor 100, and which in particular may be part of the apparatus for blood treatment. The data processing unit of the controller 65 may be in the form of a general-type processor or in the form of a dedicated processor; parts of the controller 65 and/or of said data processing unit may be made by an application specific integrated circuit or through an FPGA. In one or more embodiments, the apparatus 1, sensor 100, controller 65 or method may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion. The program used to implement the methods and/or processes described herein may be provided using any programmable language, or code, e.g., a high level procedural and/or object orientated programming language or code that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the apparatus 1, sensor 100, controller 65 or method may be implemented using a computer readable storage medium, configured with a computer program, where the storage medium so configured causes the computer to operate in a specific and predefined manner to perform functions described herein. Further, in at least one embodiment, the apparatus 1, sensor 100, controller 65 or method may be described as being implemented by logic (e.g., object code) encoded in one or more non-transitory media that includes code for execution and, when executed by a processor, is operable to perform operations such as the methods, processes, and/or functionality described herein. The controller 65 may be, for example, any fixed or mobile computer system (e.g., a controller, a microcontroller, a personal computer, mini computer, etc.). The exact configuration of the controller 65 is not limiting, and essentially any device capable of providing suitable computing capabilities and control capabilities (e.g., graphics processing, control of extracorporeal blood treatment apparatus, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by controller 65 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by an operator. In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the apparatus, sensor, processes or programs (e.g., the functionality provided by such apparatus, sensor, processes or programs) described herein. The methods and/or logic described in this disclosure, including those attributed to the sensor and/or to the apparatus and/or to the controller, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry. Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components or integrated within common or separate hardware or software components. When implemented in software, the functionality ascribed to the controller, sensor, apparatus and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

The invention claimed is:

1. An apparatus for extracorporeal blood treatment comprising:
 a blood pump configured to pump blood;
 a blood circuit comprising:
  a filtration unit having a primary chamber and a secondary chamber separated by a semi-permeable membrane,
  a blood withdrawal line having a first end connected to an inlet of the primary chamber, and
  a blood return line having a first end connected to an outlet of the primary chamber,
  wherein the blood withdrawal line has a second end provided with an arterial connector, wherein the blood return line has a second end provided with a venous connector, wherein said arterial connector and said venous connector are configured to be connected to a vascular access of a patient, wherein said blood circuit is configured to be interfaced with the blood pump for controlling a flow of the blood in the blood circuit, and wherein the blood circuit comprises an extracorporeal segment; and
 a non-invasive heartbeat sensor configured and arranged to determine one or both of a heartbeat in the extracorporeal segment and a heart rate in the extracorporeal segment, wherein said non-invasive heartbeat sensor comprises:
  at least one source for directing an optical signal towards the blood flowing in the extracorporeal segment, the optical signal being directed along an emission axis,
  detectors placed at different radial directions, or arranged at different angular degrees, with respect to the emission axis of the at least one source to collect a reflected signal, a scattered signal, and a transmitted signal depending on their respective position, and wherein each detector is configured to receive an optical informative signal comprising the optical signal emitted by said at least one source after passing at least partially through the blood flowing in the extracorporeal segment, wherein each detector is configured to emit a respective output signal related to the received optical informative signal, and
 a controller configured to:
  receive the respective output signals from the detectors,
  at least one of retrieve a heartbeat frequency and detect a heart rate value based on a predetermined number of the output signals, and
  process the output signals based on the optical informative signal as altered at least in its amplitude, by a flow perturbation of the blood flowing in the extracorporeal segment, wherein said flow perturbation is at least partially generated by flow impulses originated by a beating heart.

2. The apparatus according to claim 1, wherein said controller is further configured to:
 electronically calculate a transformation of at least one reference part of one or more of the output signals from a time domain towards a frequency domain;
 obtain an informative signal spectrum or an output signal spectrum corresponding to the informative signal spectrum;
 determine if at least one pump is forcing fluid circulation into said extracorporeal segment;
 if the at least one pump is forcing fluid circulation into said extracorporeal segment, then identify and discard a first peak of amplitude in said informative signal spectrum or the output signal spectrum, said first peak of amplitude corresponding to a spurious flow perturbation in said extracorporeal segment originated by the at least one pump forcing fluid circulation into said extracorporeal segment;
 electronically identify and select a first sought peak of amplitude in said informative signal spectrum or output signal spectrum subsequent to said discarding, said selected first sought peak of amplitude calculated through an identification of a second sought peak of amplitude in the informative signal spectrum or in the output signal spectrum, wherein said second sought peak corresponds to a subsequent harmonic of said first sought peak of amplitude; and
 electronically assign, to at least one of a provisional heartbeat and the heartbeat frequency, a frequency corresponding to the first sought peak of amplitude.

3. The apparatus according to claim 2, wherein said controller is further configured to:
 electronically load frequency values corresponding to a first lower frequency region and to at least one second upper frequency region, the at least one second upper frequency region laying above said first lower frequency region;
 store and set an upper frequency value of said first lower frequency region below a frequency threshold for non-physiological cardiac pulses; and
 process the one or more output signals, wherein processing the one or more output signals includes (i) filtering out a portion of said informative signal spectrum or the output signal spectrum corresponding to the first lower frequency region, or (ii) discarding any peak of amplitude lying in said first lower frequency region, so that the identification and discarding of the first peak of amplitude and the electronic selection of the first sought peak of amplitude is performed in said at least one second upper frequency region.

4. The apparatus according to claim 2, wherein processing the one or more output signals comprises low-pass filtering through a filter stage the one or more output signals at a predetermined frequency below 10 Hz, wherein the low-pass filtering is performed before electronically calculating the transformation of the at least one reference part of the one or more output signals from the time domain towards the frequency domain.

5. The apparatus according to claim 2, wherein the identification of the second sought peak of amplitude is performed by searching a peak of amplitude in the informative signal spectrum or in the output signal spectrum corresponding at a frequency corresponding to a double of the frequency of the first sought peak of amplitude.

6. The apparatus according to claim 2, wherein, in electronically processing the one or more output signals of said detectors, said controller is configured to perform an electronic selection of a reference window of output signal sampling, said reference window having a predetermined length less than one minute long, wherein a portion of the respective output signal constitutes the at least one reference part of the respective output signal, and wherein the electronic calculation of the transformation of the at least part of the respective output signal (i) is performed on said at least one reference part of the respective output signal and (ii) is performed after the windowing.

7. The apparatus according claim 3, wherein said identification of at least one of the first peak of amplitude, the first sought peak of amplitude, and the second sought peak of amplitude is performed through an application of a peak detection algorithm on at least part of said informative signal spectrum or the output signal spectrum, wherein the peak detection algorithm comprises:
identifying a part of the informative signal spectrum or the output signal spectrum, said part corresponding to the at least one second upper frequency region;
electronically calculating a derivative of the informative signal spectrum or the output signal spectrum obtaining a derivative spectrum; and
performing a subsequent electronic search and selection of at least one frequency, wherein said derivative spectrum changes sign from a positive value to a negative value proceeding in increasing a frequency of analysis, for identifying positive peaks, a frequency at which said derivative spectrum changes sign from a positive value to a negative value corresponding to said peak.

8. The apparatus according to claim 7, wherein the peak detection algorithm for which the controller is configured to run comprises searching for local relative maximum amplitude points in said informative signal spectrum or the output signal spectrum, said part corresponding to the at least one second upper frequency region by using moving window signal processing on the informative signal spectrum or the output signal spectrum, and a further selection of frequencies corresponding to said local relative maximum amplitude points as a frequency at which a peak occurs.

9. The apparatus according to claim 7, wherein the peak detection algorithm comprises defining a moving window of a predetermined amplitude within at least a part of the informative signal spectrum or the output signal spectrum, said part corresponding to the at least one second upper frequency region, and electronically defining a plurality of positions for said moving window within said at least the part of the informative signal spectrum or the output signal spectrum, and for each of said positions, electronically calculating a maximum amplitude of the informative signal spectrum or the output signal spectrum within said moving window, and electronically extracting and storing the frequency corresponding to said maximum amplitude.

10. The apparatus according to claim 1, wherein the controller is configured to process one or more of the output signals of said detectors with a pump-associated signal having a shape that is cyclic and repeated in time, and is correlated to a pump cycle point, so as to obtain a corresponding result signal which includes a spectrum having an enhancement of components or of peaks relating to the heartbeat or to the heart rate with respect to the components or the peaks associated with an operation of a pump of said apparatus, and wherein the controller is configured to multiply the one or more output signals of said detectors with said pump-associated signal so as to make a result signal produced in an output of said processing cyclically zeroed in correspondence of portions of times wherein said pump provides pulses in at least said extracorporeal segment.

11. The apparatus according to claim 10, wherein the controller is configured to calculate an average magnitude of said result signal across a predetermined time length window of analysis, and is further configured to perform a subsequent subtraction of said average magnitude to at least a portion of said result signal, a portion wherein said result signal was not zeroed due to the multiplication, thus producing an averaged signal constituting a reference part of the one or more output signals to which at least a transformation from a time domain to a frequency domain is performed.

12. The apparatus according to claim 10, wherein said controller is configured for:
selecting a plurality of reference parts of the one or more output signals by electronically selecting through a sampling window a plurality of portions of said one or more output signals that are not overlapped in time;
performing a transformation from a time domain towards a frequency domain,
obtaining a plurality of informative signal spectrums or a plurality of output signal spectrums related to the corresponding plurality of informative signal spectrums for each of said plurality of reference parts of the one or more signals; and
for each informative signal spectrum or output signal spectrum of said plurality of informative signal and output signal spectrums:
identifying and discarding a first noise peak of amplitude in said informative signal spectrum or the output signal spectrum, said first noise peak of amplitude corresponding to at least partially to a spurious flow perturbation in said extracorporeal segment being originated by at least one pump forcing fluid circulation into at least said extracorporeal segment,
performing an electronic identification and subsequent selection of a first sought peak of amplitude in said informative signal spectrum or the output signal spectrum after said discarding has taken place, said selection being electronically calculated through an identification of a second sought peak of amplitude in the informative signal spectrum or in the output signal spectrum, the second peak corresponding to a second harmonics of said first sought peak of amplitude,
electronically assigning, to a provisional heartbeat and/or the heartbeat frequency, a frequency corresponding to the first sought peak of amplitude, and
calculating at least one of a definitive heartbeat and the heartbeat frequency according to a plurality of provisional heartbeat and/or heartbeat frequency values obtained for each of said informative signal spectrum or the output signal spectrum, wherein the definitive heartbeat and/or heartbeat frequency is calculated in accordance with an average calculation among the plurality of provisional heartbeat and/or heartbeat frequency values obtained for each of said informative signal spectrum or the output signal spectrum.

13. The apparatus according to claim 1, wherein said controller is configured to activate an alarm signal if one of the following conditions is met:
said controller does not retrieve any heartbeat frequency;
said controller does not detect any heart rate value;

said controller, after having retrieved at least temporarily said heartbeat frequency and/or heart rate value from said optical informative signal, in a subsequent time, does not retrieve any heartbeat frequency, while in a presence of said optical informative signal; or said controller, after having retrieved at least temporarily said heartbeat frequency and/or the heart rate value from said optical informative signal, in a subsequent time, does not detect any heart rate value, while in the presence of said optical informative signal.

14. The apparatus according to claim 1, wherein the at least one source comprises an optic electromagnetic radiation emitter in the form of either:

a single-wavelength, multimode and non-coherent, LED; or a single-wavelength LASER or SLED.

15. The apparatus according to claim 1, wherein the at least one source comprises an optic electromagnetic radiation emitter in the form of a multiple wavelength emitter being either:

a multiple wavelength LED, or a combination of plurality of single-wavelength LASERs or SLEDs.

16. The apparatus according to claim 1, wherein the non-invasive heartbeat sensor further comprises:

an optic fiber having one end coupled to the at least one source and another end placed to direct the optical signal towards the blood along at least said emission axis;

wherein said detectors include one or more of (i) a first detector placed at about 180° with respect to the emission axis of the at least one source, (ii) a second detector placed at about 90° with respect to the emission axis of the at least one source, (iii) a third detector placed at about 45° with respect to the emission axis of the at least one source, or (iv) a fourth detector placed at about 0° with respect to the emission axis of the at least one source; and a housing having one portion that is counter-shaped to said extracorporeal segment, the housing being made of two or more pieces and defining a through passage that is counter-shaped to an outer shape of the extracorporeal segment to house the extracorporeal segment inside the through passage, each detector including a respective end placed at the counter-shaped portion facing the extracorporeal segment in a coupling condition of the housing with the extracorporeal segment, the at least one source including an end placed at the counter-shaped portion facing the extracorporeal segment in a coupling condition of the housing with the extracorporeal segment; and wherein each detector includes an optic fiber, one end of the optic fiber being arranged in correspondence of the extracorporeal segment and being fixed to the housing, the end of the optic fiber being placed at the counter-shaped portion and facing the extracorporeal segment in a coupling condition of the housing with the extracorporeal segment.

17. The apparatus according to claim 1, wherein the at least one source comprises a multiple wavelength emitter having a plurality of optical radiation sources with peak wavelengths in red and infrared bands, and wherein at least an illuminating peak wavelength of the at least one source is between 0.7 µm and 1000 µm.

18. The apparatus according to claim 1, wherein the at least one source is configured to transmit composite optical radiation comprising a first component of optical radiation centered on a first frequency window comprising a first wavelength, and a second component of optical radiation centered on a second frequency window comprising a second wavelength, with a third component of optical radiation centered on a third frequency window comprising a third wavelength, and with a fourth component of optical radiation centered on a fourth frequency window comprising a fourth wavelength, wherein said first, second, third, and fourth frequency windows are at least partially not superimposed in frequency.

19. The apparatus according to claim 18, wherein the detectors comprise at least a first detector configured to receive the first component of optical radiation at the first wavelength, a second detector configured to receive the second component of optical radiation at the second wavelength, a third detector configured to receive the third component of optical radiation at the third wavelength, and a fourth detector configured to receive the fourth component of optical radiation at the fourth wavelength.

20. The apparatus according to claim 18, wherein said at least one source is configured to transmit said optical radiation in a direction transversal to a main development axis of said extracorporeal segment, and wherein the detectors are configured to receive the optical signal emitted by the at least one source along a direction that is transversal to the main development axis of said extracorporeal segment.

21. The apparatus according to claim 1, wherein the extracorporeal segment of the blood circuit includes a tube portion, said detectors and said at least one source being disposed around said tube portion at different angular degrees around a same cross section, said tube portion having a circular cross section.

22. The apparatus according to claim 1, wherein the non-invasive heartbeat sensor is directly constrained to an external portion of the extracorporeal segment having circular inner and outer sections, wherein said extracorporeal segment is made of a flexible material with a predetermined degree of transparency to optical radiations.

* * * * *